US011633370B2

(12) United States Patent
Roberts, II et al.

(10) Patent No.: US 11,633,370 B2
(45) Date of Patent: Apr. 25, 2023

(54) USE OF SCAVENGERS OF REACTIVE GAMMA-KETOALDEHYDES TO EXTEND CELL LIFESPAN AND HEALTHSPAN

(71) Applicant: Vanderbilt University, Nashville, TN (US)

(72) Inventors: L. Jackson Roberts, II, Gallatin, TN (US); Thuy T. Nguyen, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/314,851

(22) PCT Filed: Jul. 6, 2017

(86) PCT No.: PCT/US2017/040982
§ 371 (c)(1),
(2) Date: Jan. 2, 2019

(87) PCT Pub. No.: WO2018/009720
PCT Pub. Date: Jan. 11, 2018

(65) Prior Publication Data
US 2019/0240170 A1    Aug. 8, 2019

Related U.S. Application Data

(60) Provisional application No. 62/359,183, filed on Jul. 6, 2016.

(51) Int. Cl.
*A61K 31/135*    (2006.01)
*A61K 31/44*    (2006.01)
*A61P 39/06*    (2006.01)
*A61K 31/137*    (2006.01)

(52) U.S. Cl.
CPC .......... *A61K 31/135* (2013.01); *A61K 31/137* (2013.01); *A61K 31/44* (2013.01); *A61P 39/06* (2018.01)

(58) Field of Classification Search
CPC .... A61K 31/135; A61K 31/137; A61K 31/44; A61P 39/06
See application file for complete search history.

(56) References Cited

U.S. PATENT DOCUMENTS

| 7,705,054 B1 * | 4/2010 | Roberts, II | ............. | A61K 31/44 |
| | | | | 514/649 |
| 2012/0157501 A1 | 6/2012 | Roberts et al. | | |
| 2014/0256774 A1 | 9/2014 | Roberts et al. | | |

OTHER PUBLICATIONS

Wikipedia page on cell death; downloaded Mar. 23, 2020 (Year: 2020).*
Wikipedia page for the sirtuin (downloaded Aug. 20, 2020) (Year: 2020).*
Gizem Donmez, The Effects of SIRT1 on Alzheimer's Disease Models, International Journal of Alzheimer's Disease, vol. 2012, Article ID 509529, 3 pages, doi:10.1155/2012/509529 (Year: 2012).*
Davies et al. Pyridoxamine Analogues Scavenge Lipid-Derived Gamma-ketoaldehydes and Protect against H2O2-Mediated Cytotoxicity in Biochemistry, 2006, vol. 45, pp. 15756-15767.
Gardner, H.W., Oxygen radical chemistry of polyunsaturated fatty acids. Free Radic Biol Med, 1989. 7(1): p. 65-86.
Niki, E., Lipid peroxidation: physiological levels and dual biological effects. Free Radic Biol Med, 2009. 47(5): p. 469-84.
Halliwell, B. and J.M. Gutteridge, Role of free radicals and catalytic metal ions in human disease: an overview. Methods Enzymol, 1990. 186: p. 1-85.
Gutteridge, J.M., Lipid peroxidation and antioxidants as biomarkers of tissue damage. Clin Chem, 1995. 41(12 Pt 2): p. 1819-28.
Butterfield, D.A., beta-Amyloid-associated free radical oxidative stress and neurotoxicity: implications for Alzheimer's disease. Chem Res Toxicol, 1997. 10(5): p. 495-506.
Poon, H.F., et al., Free radicals and brain aging. Clin Geriatr Med, 2004. 20(2): p. 329-59.
Comporti, M., Lipid peroxidation and biogenic aldehydes: from the identification of 4-hydroxynonenal to further achievements in biopathology. Free Radic Res, 1998. 28(6): p. 623-35.
Morrow, J.D., et al., A series of prostaglandin F2-like compounds are produced in vivo in humans by a non-cyclooxygenase, free radical-catalyzed mechanism. Proc Natl Acad Sci U S A, 1990. 87(23): p. 9383-7.
Brame, C.J., et al., Identification of extremely reactive gamma-ketoaldehydes (isolevuglandins) as products of the isoprostane pathway and characterization of their lysyl protein adducts. J Biol Chem, 1999. 274(19): p. 13139-46.
Boutaud, O., et al., Characterization of the lysyl adducts formed from prostaglandin H2 via the levuglandin pathway. Biochemistry, 1999. 38(29): p. 9389-96.
Iyer, R.S., S. Ghosh, and R.G. Salomon, Levuglandin E2 crosslinks proteins. Prostaglandins, 1989. 37(4): p. 471-80.
Salomon, R.G., et al., Isolevuglandin-protein adducts in humans: products of free radical-induced lipid oxidation through the isoprostane pathway. Biochim Biophys Acta, 2000. 1485(2-3): p. 225-35.
Zagol-Ikapitte, I., et al., Prostaglandin H(2)-derived adducts of proteins correlate with Alzheimer's disease severity. J Neurochem, 2005. 94(4): p. 1140-5.
Kirabo, A., et al., DC isoketal-modified proteins activate T cells and promote hypertension. J Clin Invest, 2014. 124(10): p. 4642-56.
Davies, S.S., et al., Effects of reactive gamma-ketoaldehydes formed by the isoprostane pathway (isoketals) and cyclooxygenase pathway (levuglandins) on proteasome function. Faseb j, 2002. 16(7): p. 715-7.
Boutaud, O., et al., Prostaglandin H2 (PGH2) accelerates formation of amyloid beta1-42 oligomers. J Neurochem, 2002. 82(4): p. 1003-6.
Murthi, K.K., R.G. Salomon, and H. Sternlicht, Levuglandin E2 inhibits mitosis and microtubule assembly. Prostaglandins, 1990. 39(6): p. 611-22.

(Continued)

*Primary Examiner* — Kortney L. Klinkel
*Assistant Examiner* — Jason Deck
(74) *Attorney, Agent, or Firm* — Stites & Harbison PLLC; Richard S. Myers, Jr.

(57) ABSTRACT

Methods and compounds for use in promoting survival of at least one eukaryotic cell, wherein the compounds are effective as gamma-ketoaldehyde scavengers.

4 Claims, 7 Drawing Sheets

(56) References Cited

OTHER PUBLICATIONS

Schmidley, J.W., et al., Brain tissue injury and blood-brain barrier opening induced by injection of LGE2 or PGE2. Prostaglandins Leukot Essent Fatty Acids, 1992. 47(2): p. 105-10.

Amarnath, V., et al., Pyridoxamine: An Extremely Potent Scavenger of 1,4-Dicarbonyls. Chemical Research in Toxicology, 2004. 17(3): p. 410-415.

Davies, S.S., et al., Pyridoxamine analogues scavenge lipid-derived gamma-ketoaldehydes and protect against H2O2-mediated cytotoxicity. Biochemistry, 2006 45(51): p. 15756-67.

Zagol-Ikapitte, I., et al., Determination of the Pharmacokinetics and Oral Bioavailability of Salicylamine, a Potent γ-Ketoaldehyde Scavenger, by LC/MS/MS. Pharmaceutics, 2010. 2(1): p. 18.

Davies, S.S., et al., Treatment with a γ-ketoaldehyde scavenger prevents working memory deficits in hApoE4 mice. Journal of Alzheimer's Disease, 2011. 27(1): p. 49-59.

Rose, M.R., et al., What is Aging? Frontiers in Genetics, 2012. 3: p. 134.

Jin, K., Modern Biological Theories of Aging. Aging and Disease, 2010. 1(2): p. 72-74.

Kirkwood, T.B., Understanding the odd science of aging. Cell, 2005. 120(4): p. 437-47.

Wilkinson, D.S., R.C. Taylor, and A. Dillin, Analysis of aging in Caenorhabditis elegans. Methods Cell Biol, 2012. 107: p. 353-81.

Flatt, T., A new definition of aging? Front Genet, 2012. 3: p. 148.

Murshid, A., T. Eguchi, and S.K. Calderwood, Stress proteins in aging and life span. Int J Hyperthermia, 2013. 29(5): p. 442-7.

Haigis, M.C. and B.A. Yankner, The aging stress response. Mol Cell, 2010. 40(2): p. 333-44.

Lockshin, R.A. and J. Beaulaton, Programmed cell death. Life Sci, 1974. 15(9): p. 1549-65.

Forciea, M.A., Aging. Programmed change. Dent Clin North Am, 1989. 33(1): p. 19-22.

Gladyshev, V.N., The Free Radical Theory of Aging Is Dead. Long Live the Damage Theory! Antioxidants & Redox Signaling, 2014. 20(4): p. 727-731.

Comfort, A., Physiology, homoeostasis and ageing. Gerontologia, 1968. 14(4): p. 224-34.

Hartl, F.U., Cellular Homeostasis and Aging. Annu Rev Biochem, 2016.

Lints, F.A., The rate of living theory revisited. Gerontology, 1989. 35(1): p. 36-57.

Brys, K., J.R. Vanfleteren, and B.P. Braeckman, Testing the rate-of-living/oxidative damage theory of aging in the nematode model Caenorhabditis elegans. Exp Gerontol, 2007. 42(9): p. 845-51.

Harman, D., Aging: a theory based on free radical and radiation chemistry. J Gerontol, 1956.11(3): p. 298-300.

Labbadia, J. and R.I. Morimoto, The Biology of Proteostasis in Aging and Disease. Annual review of biochemistry, 2015. 84: p. 435-464.

Maynard, S., et al., DNA Damage, DNA Repair, Aging, and Neurodegeneration. Cold Spring Harb Perspect Med, 2015. 5(10).

Donmez, G. and L. Guarente, Aging and disease: connections to sirtuins. Aging Cell, 2010. 9(2): p. 285-90.

Lin, S.J., P.A. Defossez, and L. Guarente, Requirement of NAD and SIR2 for life-span extension by calorie restriction in *Saccharomyces cerevisiae*. Science, 2000. 289(5487): p. 2126-8.

Bell, E.L. and L. Guarente, The SirT3 divining rod points to oxidative stress. Mol Cell, 2011. 42(5): p. 561-8.

Kaeberlein, M., M. McVey, and L. Guarente, The SIR2/3/4 complex and SIR2 alone promote longevity in *Saccharomyces cerevisiae* by two different mechanisms. Genes Dev, 1999. 13(19): p. 2570-80.

Guarente, L., Sir2 links chromatin silencing, metabolism, and aging. Genes Dev, 2000. 14(9): p. 1021-6.

Tissenbaum, H.A. and L. Guarente, Increased dosage of a sir-2 gene extends lifespan in Caenorhabditis elegans. Nature, 2001. 410(6825): p. 227-30.

Rogina, B. and S.L. Helfand, Sir2 mediates longevity in the fly through a pathway related to calorie restriction. Proc Natl Acad Sci U S A, 2004. 101(45): p. 15998-6003.

Hashimoto, Y., S. Ookuma, and E. Nishida, Lifespan extension by suppression of autophagy genes in Caenorhabditis elegans. Genes Cells, 2009. 14(6): p. 717-26.

Lee, G.D., et al., Dietary deprivation extends lifespan in Caenorhabditis elegans. Aging Cell, 2006. 5(6): p. 515-24.

Wang, Y. and H.A. Tissenbaum, Overlapping and distinct functions for a Caenorhabditis elegans SIR2 and DAF-16/FOXO. Mech Ageing Dev, 2006. 127(1): p. 48-56.

Bansal, A., et al., Uncoupling lifespan and healthspan in Caenorhabditis elegans longevity mutants. Proc Natl Acad Sci U S A, 2015. 112(3): p. E277-86.

Clokey, G.V. and L.A. Jacobson, The autofluorescent "lipofuscin granules" in the intestinal cells of Caenorhabditis elegans are secondary lysosomes. Mech Ageing Dev, 1986. 35(1): p. 79-94.

Yin, D., Biochemical basis of lipofuscin, ceroid, and age pigment-like fluorophores. Free Radic Biol Med, 1996. 21(6): p. 871-88.

Wolkow, C.A., Identifying factors that promote functional aging in Caenorhabditis elegans. Exp Gerontol, 2006. 41(10): p. 1001-6.

Huang, C., C. Xiong, and K. Kornfeld, Measurements of age-related changes of physiological processes that predict lifespan of Caenorhabditis elegans. Proc Natl Acad Sci U S A, 2004. 101(21): p. 8084-9.

Herndon, L.A., et al., Stochastic and genetic factors influence tissue-specific decline in ageing C. elegans. Nature, 2002. 419(6909): p. 808-14.

Davies, S.S., et al., Measurement of chronic oxidative and inflammatory stress by quantification of isoketal/levuglandin gamma-ketoaldehyde protein adducts using liquid chromatography tandem mass spectrometry. Nat Protoc, 2007. 2(9): p. 2079-91.

Zhu, A.Y., et al., Plasmodium falciparum Sir2A preferentially hydrolyzes medium and long chain fatty acyl lysine. ACS Chemical Biology, 2012. 7(1): p. 155-159.

Choudhary, C., et al., The growing landscape of lysine acetylation links metabolism and cell signalling. Nat Rev Mol Cell Biol, 2014. 15(8): p. 536-50.

Bokov, A., A. Chaudhuri, and A. Richardson, The role of oxidative damage and stress in aging. Mech Ageing Dev, 2004. 125(10-11): p. 811-26.

Tao, R., et al., Sirt3-mediated deacetylation of evolutionarily conserved lysine 122 regulates MnSOD activity in response to stress. Mol Cell, 2010. 40(6): p. 893-904.

Someya, S., et al., Sirt3 mediates reduction of oxidative damage and prevention of age-related hearing loss under caloric restriction. Cell, 2010. 143(5): p. 802-12.

Caito, S., et al., SIRT1 is a redox-sensitive deacetylase that is post-translationally modified by oxidants and carbonyl stress. The FASEB Journal, 2010. 24(9): p. 3145-3159.

Nguyen, T.T. and M. Aschner, F3-Isoprostanes as a Measure of in vivo Oxidative Damage in Caenorhabditis elegans. Curr Protoc Toxicol, 2014. 62: p. 11.17.1-11.17.13.

Labuschagne, C.F., et al., Quantification of in vivo oxidative damage in Caenorhabditis elegans during aging by endogenous F3-isoprostane measurement. Aging Cell, 2013. 12(2): p. 214-23.

Gao, L., et al., Formation of F-ring isoprostane-like compounds (F3-isoprostanes) in vivo from eicosapentaenoic acid. J Biol Chem, 2006. 281(20): p. 14092-9.

Wallace, D.C., A mitochondrial paradigm of metabolic and degenerative diseases, aging, and cancer: a dawn for evolutionary medicine. Annu Rev Genet, 2005. 39: p. 359-407.

Finkel, T. and N.J. Holbrook, Oxidants, oxidative stress and the biology of ageing. Nature, 2000. 408(6809): p. 239-47.

Ryan, M.T. and N.J. Hoogenraad, Mitochondrial-nuclear communications. Annu Rev Biochem, 2007. 76: p. 701-22.

Gershon, H. and D. Gershon, Paradigms in aging research: a critical review and assessment. Meeh Ageing Dev, 2000. 117(1-3): p. 21-8.

Alic, N., et al., Interplay of dFOXO and two ETS-family transcription factors determines lifespan in *Drosophila melanogaster*. PLoS Genet, 2014. 10(9): p. e1004619.

Thyagarajan, B., et al., ETS-4 is a transcriptional regulator of life span in Caenorhabditis elegans. PLoS Genet, 2010. 6(9): p. e1001125.

(56) References Cited

OTHER PUBLICATIONS

Chin, R.M., et al., The metabolite alpha-ketoglutarate extends lifespan by inhibiting ATP synthase and TOR. Nature, 2014. 510(7505): p. 397-401.
Rauthan, M., et al., A Mutation in Caenorhabditis elegans NDUF-7 Activates the Mitochondrial Stress Response and Prolongs Lifespan via ROS and CED-4. G3 (Bethesda), 2015. 5(8): p. 1639-48.
McCormack, S., et al., Pharmacologic targeting of sirtuin and PPAR signaling improves longevity and mitochondrial physiology in respiratory chain complex I mutant Caenorhabditis elegans. Mitochondrion, 2015. 22: p. 45-59.
Edwards, C., et al., Mechanisms of amino acid-mediated lifespan extension in Caenorhabditis elegans. BMC Genet, 2015. 16: p. 8.
Furuhashi, T., et al., I-arginine, an active component of salmon milt nucleoprotein, promotes thermotolerance via Sirtuin in Caenorhabditis elegans. Biochem Biophys Res Commun, 2016. 472(1): p. 287-91.
Pant, A., et al., Beta-caryophyllene modulates expression of stress response genes and mediates longevity in Caenorhabditis elegans. Exp Gerontol, 2014. 57: p. 81-95.
Guo, X. and L.R. Garcia, SIR-2.1 integrates metabolic homeostasis with the reproductive neuromuscular excitability in early aging male Caenorhabditis elegans. Elife, 2014. 3: p. e01730.
Calabrese, E.J., et al., What is hormesis and its relevance to healthy aging and longevity? Biogerontology, 2015. 16(6): p. 693-707.
Monaghan, P. and M.F. Haussmann, The positive and negative consequences of stressors during early life. Early Hum Dev, 2015. 91(11): p. 643-7.
Sun, S., et al., Translational profiling identifies a cascade of damage initiated in motor neurons and spreading to glia in mutant SOD1-mediated ALS. Proceedings of the National Academy of Sciences of the United States of America, 2015. 112(50): p. E6993-E7002.
McMaster, W.G., et al., Inflammation, Immunity, and Hypertensive End-Organ Damage. Circulation research, 2015. 116(6): p. 1022-1033.
Wu, J., et al., Immune activation caused by vascular oxidation promotes fibrosis and hypertension. J Clin Invest, 2016. 126(1): p. 50-67.
Egnatchik, et a., Loss of normal Bone Morphogenetic Protein Receptor Type 2 signaling drives pulmonary hypertension through metabolic reprogramming toward glutaminolysis. In Press, 2016.
Wang, H., et al., NRF2 activation by antioxidant antidiabetic agents accelerates tumor metastasis. Sci Transl Med, 2016. 8(334): p. 334ra51.
Prasad, S., S.C. Gupta, and A.K. Tyagi, Reactive oxygen species (ROS) and cancer: Role of antioxidative nutraceuticals, Cancer Letters 387 (2017) 95-105.
Lewis, J.A. and J.T. Fleming, Basic culture methods. Methods Cell Biol, 1995. 48: p. 3-29.
Mitchell, D.H., et al., Synchronous growth and aging of Caenorhabditis elegans in the presence of fluorodeoxyuridine. J Gerontol, 1979. 34(1): p. 28-36.
Gavet, O. and J. Pines, Progressive activation of CyclinB1-Cdk1 coordinates entry to mitosis. Developmental cell, 2010. 18(4): p. 533-543.
Bratic, I., et al., Mitochondrial DNA level, but not active replicase, is essential for Caenorhabditis elegans development. Nucleic Acids Res, 2009. 37(6): p. 1817-28.
Amarnath, V., et al., A Simplified Synthesis of the Diastereomers of Levuglandin E2. Synthetic Communications, 2005. 35(3): p. 397-408.
Milne, G.L., et al., Quantification of F2-isoprostanes as a biomarker of oxidative stress. Nat Protoc, 2007. 2(1): p. 221-6.
Latif, S., et al., Fluorescence Polarization in Homogeneous Nucleic Acid Analysis II: 5'-Nuclease Assay. Genome Research, 2001. 11(3): p. 436-140.
Nguyen, et al., Reactive y-Ketoaldehyde scavengers extended lifespan and healthspan in C. elegans through protein-level interactions with Sir2.1 and Ets-7; Free Radical Biology and Medicine, vol. 87, Oct. 2015, p. S131.
Zagol-Ikapitte, et al., Characterization of Scavengers of γ-Ketoaldehydes That Do Not Inhibit Prostaglandin Biosynthesis, Chem. Res. Toxicol. 2010, 23, 240-250.

* cited by examiner

USE OF SCAVENGERS OF REACTIVE GAMMA-KETOALDEHYDES TO EXTEND CELL LIFESPAN AND HEALTHSPAN

PRIOR APPLICATIONS

This application is a § 371 National State Application of PCT/US2017/040982 filed Jul. 6, 2017, which claims the benefit of U.S. Provisional Application Ser. No. 62/359,183, filed Jul. 6, 2016, the entire disclosure of which is incorporated herein by this reference.

GOVERNMENT SUPPORT

This invention was made with government support under grant numbers HL121174 and HL095797 awarded by the National Institutes of Health. The government has rights to this invention.

DESCRIPTION OF THE INVENTION

Isoketals (IsoKs) are highly reactive γ-ketoaldehyde products of lipid peroxidation that covalently adduct lysine side chains in proteins, impairing their function. Using *C. elegans* as a model organism, the present inventors have discovered that IsoKs contribute to molecular aging through adduction and inactivation of specific protein targets, and that this process can be abrogated using compounds of the present invention, including salicylamine (SA), a selective IsoK scavenger.

The present inventors have discovered that treatment with at least one compound of the present invention extends adult nematode longevity by nearly 67% and prevents multiple deleterious age-related biochemical and functional changes.

Examples of compounds of the present invention include, but are not limited to, compounds selected from the formula:

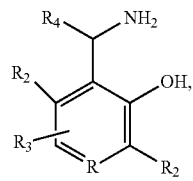

wherein: R is N or C; $R_2$ is independently H, substituted or unsubstituted alkyl; $R_3$ is H, halogen, alkoxy, hydroxyl, nitro; $R_4$ is H, substituted or unsubstituted alkyl, carboxyl; and pharmaceutically acceptable salts thereof.

The compound may be chosen from:

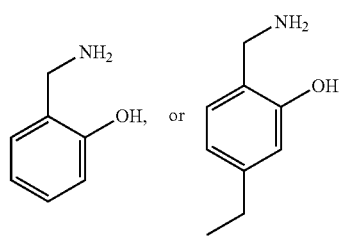

or a pharmaceutically acceptable salt thereof.

The compound may also be chosen from:

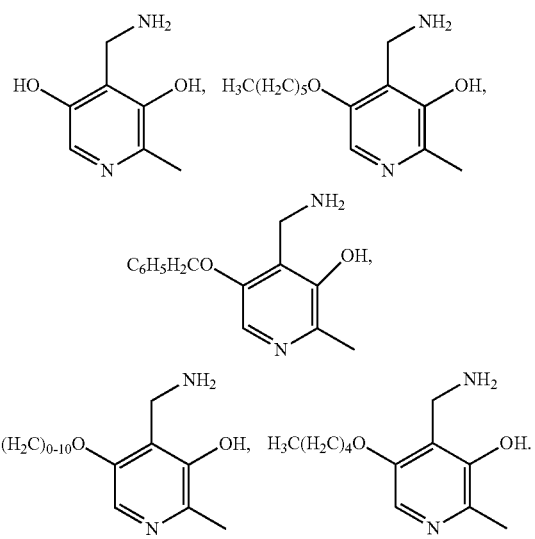

or a pharmaceutically acceptable salt thereof.

The compounds or analogs may also be chosen from:

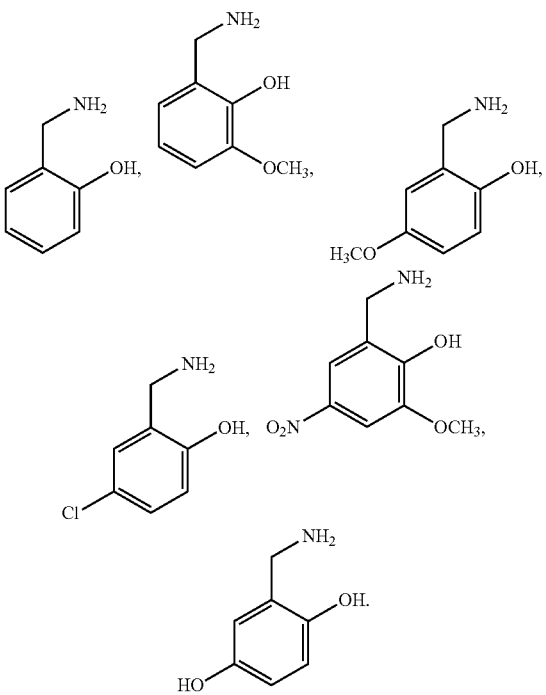

or a pharmaceutically acceptable salt thereof.

The compounds may also be chosen from:

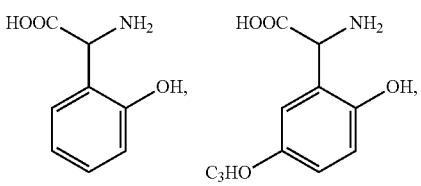

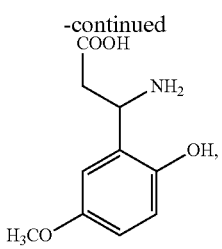

or a pharmaceutically acceptable salt thereof.

The compounds may also be chosen from

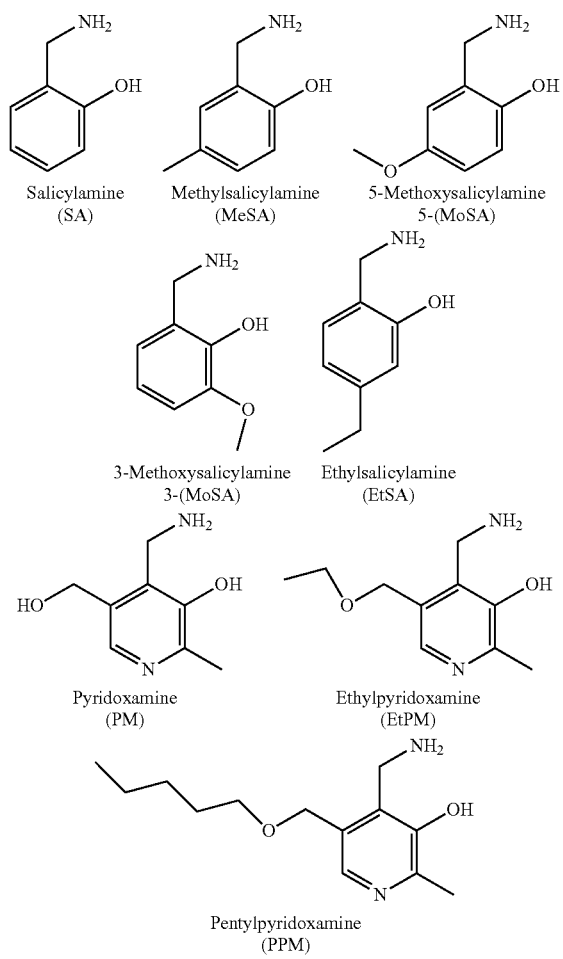

or a pharmaceutically acceptable salt thereof.

Accordingly, one embodiment of the present invention is a method for promoting survival of a cell, comprising administering to a patient in need thereof an effective amount of at least one γ-KA scavenger compound of the present invention, or a pharmaceutically acceptable salt thereof. Preferably, the compound is salicylamine.

Another embodiment of the present invention is a method for treating or preventing a disease or disorder associated with cell death or aging in a subject, comprising administering to a patient in need thereof an effective amount of at least one γ-KA scavenger compound of the present invention, or a pharmaceutically acceptable salt thereof. Preferably, the compound is salicylamine.

Another embodiment of the present invention is a method for treating or preventing a neurodegenerative disorder in a subject, including Alzheimer's disease, comprising administering to a subject in need thereof a therapeutically effective amount of at least one γ-KA scavenger compound of the present invention, or a pharmaceutically acceptable salt thereof. Preferably, the compound is salicylamine.

Another embodiment of the present invention is a method for increasing muscle adenosine triphosphate (ATP) levels in a subject, comprising administering to a subject in need thereof a therapeutically effective amount of at least one γ-KA scavenger compound of the present invention, or a pharmaceutically acceptable salt thereof. Preferably, that compound is salicylamine.

Another embodiment of the present invention is a method of treating an inflammatory autoimmune response, comprising administering to a subject in need thereof a therapeutically effective amount of at least one γ-KA scavenger compound of the present invention, or a pharmaceutically acceptable salt thereof. Preferably, that compound is salicylamine.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. As can be seen herein, there is overlap in the definition of treating and preventing.

As used herein, the term "diagnosed" means having been subjected to a physical examination by a person of skill, for example, a physician, and found to have a condition that can be diagnosed or treated by the compounds, compositions, or methods disclosed herein. As used herein, the phrase "identified to be in need of treatment for a disorder," or the like, refers to selection of a subject based upon need for treatment of the disorder. For example, a subject can be identified as having a need for treatment of a disorder (e.g., a disorder related to inflammation) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "scavenger" or "scavenging" refers to a chemical substance that can be administered in order to remove or inactivate impurities or unwanted reaction products. For example, the isoketals irreversibly adduct specifically to lysine residues on proteins. The isoketal scavengers of the present invention react with isoketals before they adduct to the lysine residues. Accordingly, the compounds of the present invention "scavenge" isoketals, thereby preventing them from adducting to proteins.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by a formula $(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1\text{-}OA^2$ or $—OA^1\text{-}(OA^2)_a\text{-}OA^3$, where "a" is an integer of from 1 to 200 and $A^1$, $A^2$, and $A^3$ are alkyl and/or cycloalkyl groups.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "hydroxyl" as used herein is represented by a formula —OH.

The term "nitro" as used herein is represented by a formula $—NO_2$.

The term "pharmaceutically acceptable" describes a material that is not biologically or otherwise undesirable, i.e., without causing an unacceptable level of undesirable biological effects or interacting in a deleterious manner.

Testing of a variety of molecular targets for SA's action revealed the sirtuin SIR-2.1 as the leading candidate. When SA was administered to a SIR-2.1 knockout strain, the effects on lifespan and healthspan extension were abolished. The SIR-2.1-dependent effects of SA were not mediated by large changes in gene expression programs or by significant changes in mitochondrial function. However, expression array analysis did show SA-dependent regulation of the transcription factor ets-7 and associated genes. In ets-7 knockout worms, SA's longevity effects were abolished, similar to sir-2.1 knockouts. However, SA dose-dependently increases ets-7 mRNA levels in non-functional SIR-2.1 mutant, suggesting that SIR-2.1 lies upstream of ets-7, and that both are necessary for SA's complete lifespan and healthspan extension.

US Published Patent Applications Nos. 2007/0037865 and 20090163476, incorporated herein by reference, disclose sirtuin-modulating compounds that may be used for increasing the lifespan of a cell, and treating and/or preventing a wide variety of diseases and disorders including, for example, sirtuin-modulating compounds for treating and/or preventing a wide variety of diseases and disorders including, for example, diseases or disorders related to aging or stress, diabetes, obesity, neurodegenerative diseases, ocular diseases and disorders, cardiovascular disease, blood clotting disorders, inflammation, cancer, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia.

Thus, one embodiment of the present invention is a method for promoting survival of a eukaryotic cell, comprising contacting the cell with a compound of the present invention, including SA, or a pharmaceutically acceptable salt thereof.

Another embodiment of the present invention is a method for treating or preventing a disease or disorder associated with cell death or aging in a subject, comprising administering to a subject in need thereof a therapeutically effective amount of a compound of the present invention, including SA, or a pharmaceutically acceptable salt thereof.

Another embodiment of the present invention is a method for treating or preventing a neurodegenerative disorder in a subject, including Alzheimer's disease, comprising administering to a subject in need thereof a therapeutically effective amount of a compound of the present invention, including SA, or a pharmaceutically acceptable salt thereof.

Another embodiment of the present invention is a method for increasing muscle ATP levels in a subject, comprising administering to a subject in need thereof a therapeutically effective amount of a compound of the present invention, including SA, or a pharmaceutically acceptable salt thereof.

BACKGROUND OF THE INVENTION

Peroxidation of polyunsaturated fatty acids is a hallmark of oxidative stress, in part due to their susceptibility to free radical attack [1, 2]. Accumulation of lipid peroxidation products has been implicated in the pathogenesis of a number of human diseases, such as atherosclerosis, cancer, and neurodegenerative diseases [3-5]. This phenomenon plays a critical role in the propagation of oxidative damage and in cell death cascades, in part through the formation of reactive aldehydes [6]. These secondary products of lipid peroxidation, which include malondialdehyde (MDA) and the reactive hydroxyl-alkenals, are known to contribute to and partially mediate the effects of lipid peroxidation [6, 7].

The present inventors have identified highly reactive levuglandin-like γ-ketoaldehydes (γ-KA, or isoketals, IsoK) comprised of 64 regio- and stereo-isomers. Isoketals are formed as products of the isoprostane pathway via rearrangement of prostaglandin $H_2$-like endoperoxide intermediates ($H_2$-isoprostanes) [8, 9]. IsoKs covalently adduct ε-amino groups in lysyl residues of proteins to form stable adducts (structurally characterized as lactam rings) and intramolecular cross-links [9-11]. IsoK-lysyl-lactam adducts have been shown to be significantly increased in atherosclerosis, end-stage renal disease, Alzheimer's disease, and as a significant contributing cause of hypertension [12-14]. While the potent cytotoxicity of IsoKs and their ability to induce protein aggregation and to disrupt enzymatic function indicate a strong pathologic potential [15-18], meaningful investigation into the extent to which formation of IsoK adducts on proteins contributes to disease requires methods to selectively reduce the formation of IsoK adducts in vivo.

To better define the biological role of isoketals in oxidative injury and potentially prevent their detrimental effects, studies were performed to identify selective scavengers of IsoKs. A lead compound, pyridoxamine (PM) was identified through initial screens [19]. Structure-activity relationship studies identified the critical moiety to be a phenolic amine with the hydroxyl group adjacent to the methyl amine. Therefore, other phenolic amines such as salicylamine (SA) are similarly potent and as selective as PM for scavenging isoketals, but are more lipophilic. SA protects cellular viability in intact cells exposed to hydrogen peroxide, with SA pre-treatment leading to 5% occurrence in cell death, compared to 95% cell death in vehicle control treated cells, which suggests that IsoKs are major effectors of oxidative mediated death [20]. SA is orally bioavailable [21], and administering SA in mice prevents the age-related loss of working memory and the development of angiotensin II-induce hypertension [14, 22]. Although preventing IsoKs from adducting to proteins has broad and remarkable beneficial biological effects, the precise molecular processes that are being altered by the IsoK scavengers are not clearly defined. More precisely, the potential role that IsoKs may play in the aging process, and how IsoK scavengers may be able to influence normal aging, is an open question currently.

Aging is characterized by progressively diminishing function at the molecular, cellular, tissue, and whole organism levels [23-26]. The overall results are a gradual decline in the capacity to respond to environmental challenges and an increasing vulnerability to disease and death [27-29]. The mechanisms contributing to the multi-level, multisystem changes that are recognized as aging are a matter of debate for some. Broadly, mechanisms underlying aging can be divided into theories of programmed aging [30, 31] and theories of cumulative damage [32] and failed homeostasis [33], though it must be recognized that the two may be related [34]. At least for the cumulative damage/failed homeostasis hypotheses (e.g., "rate of living"/metabolic theory [35, 36], free radical theory [37], failed proteostasis [38], cumulative DNA damage [39], etc.), pathways controlling molecular metabolism and redox homeostasis repeatedly emerge as being central to the aging process [34]. One of the best studied pathways lying at the intersection of metabolic control, redox regulation, and aging is the sirtuin pathway.

Sirtuins are a highly conserved family of proteins that play major roles in adapting physiology to dietary extremes, as well as being implicated in countering aging and diseases associated with aging [40-42]. Sirtuins are nicotinamide adenine dinucleotide ($NAD^+$)-dependent protein deacetylases and/or ADP-ribosyltransferases. Due to the requirement of NAD for biochemical activity, sirtuins sense and respond to the metabolic status of the cell. Indeed, this is thought to be a key mechanism by which caloric restriction extends natural lifespan—namely, by increasing NAD+ availability, which increases sirtuin activity. Numerous studies in model organisms, including yeast, worms, and flies, suggest that manipulation of sirtuin Sir2 (silent information regulator 2) and its homologs can extend lifespan [41, 43-46]. Over-expression of the closest homolog to yeast Sir2 in C. elegans, sir-2.1, leads to extension of lifespan, and deletion or knockdown of the gene shortens lifespan [45, 47-49]. Although it is a family of seven mammalian sirtuins (SIRT1-7) that play various roles in the regulation of stress resistance, metabolism, and cell survival, their roles in the regulation of mammalian lifespan are still unresolved. Despite the uncertainty, many studies suggest that sirtuins regulate stress response pathways that contribute to aging and age-related diseases.

The present inventors have determined that age-related oxidant injury and accumulation of IsoKs leads to adduction and inactivation of key proteins that regulate lifespan and healthspan. Specifically, they determined that SIR-2.1 and downstream targets are inactivated by IsoK adduction, and that treatment with a scavenger of IsoKs would preserve protein function, extend natural lifespan and diminish degenerative changes in physical health. The present inventors found that treating wild-type Bristol N2 with SA, a potent scavenger of IsoKs, significantly extended lifespan and healthspan. The present inventors showed that SA's effects on longevity are dependent upon SIR-2.1, as knocking out its protein biochemical function abolished drug effect. In subsequent experiments, the present inventors have defined a SIR-2.1/ets-7 axis that is preserved by SA to regulate lifespan and healthspan along with classical markers of aging and oxidant injury, largely through maintaining proteostasis.

The oxidative stress theory of aging postulates that ROS formed by normal metabolic processes play a role in the aging process [37]. The imbalance between pro-oxidants and antioxidants leads to an accumulation of oxidative damage in a variety of macromolecules with age, resulting in a progressive loss in functional cellular processes. Given the present inventors' observation that the reactive γ-ketoaldehydes termed IsoKs play a critical role in oxidative injury by adducting to and inactivating multiple proteins, the present inventors discovered that SA administration would extend natural lifespan by scavenging IsoKs and preventing age-related inactivation of key protein targets. Starting at Day 1 of adulthood, N2 WT $C.$ $elegans$ were continuously exposed to increasing concentrations of SA until natural death (FIG. 1A). SA produced a significant dose-dependent increase in median lifespan (FIG. 1B), with 50 μM increasing median lifespan by 18% from 16 days to 19 days, 100 μM increasing lifespan by 32% from 16 days to 21 days ($p<0.05$), and 500 μM increasing median lifespan by 56% from 16 days to 25 days ($p<0.01$). These data show a significant lifespan extension effect of SA in adult WT $C.$ $elegans$.

The present inventors also demonstrated that SA administration would not only prolong natural lifespan in adult worms, but that the longer-lived worms would also exhibit prolonged healthspan—i.e., that they would be phenotypically more youthful [50]. To quantify this, the present inventors chose both a biochemical endpoint (lipofuscin autofluorescence) and a behavioral measure (pharyngeal pumping) that change predictably with aging and are associated with healthspan. The accumulation in the nematode intestinal epithelium of autofluorescent lipofuscin granules, a heterogeneous mixture of oxidized and crosslinked lipids and proteins and advanced glycation end products, is a known conserved phenomenon observed to increase with age [51, 52]. Visualization of lipofuscin granules is often used as an age-related assessment of healthspan. Lipofuscin autofluorescence were quantified over time (every 5 days) in N2 adult nematodes (10-20 per colony) in the presence of increasing doses of SA. SA response profiles were generated from integrating the area-under-the-curve (AUC) of fluorescent intensity as a function of time (FIG. 1C). Treatment with either 100 μM or 500 μM SA showed a significant reduction in age-associated lipofuscin accumulation compared with vehicle control in WT animals ($p<0.01$). For a behavioral/functional measurement of health, pharyngeal pumping rates were quantified. Worms ingest bacteria using the pharynx, requiring constant pumping by the pharyngeal bulb [53]. The rate of pharyngeal pumping declines reliably with age and has been attributed to multiple age-related processes [54, 55]. Pharyngeal pumping rates quantified in WT N2 worms established on OP50-seeded NGM agar plates with increasing concentrations of SA. The frequency of pharyngeal pumping was measured and recorded every fifth day as the animals aged. Overall, WT N2 worms showed dose-dependent protection against age-associated decline in pharyngeal pumping rate (FIG. 1D) ($p<0.05$). Taken together, these data demonstrate that SA not only dose-dependently prolongs lifespan but also healthspan when administered to adult N2 $C.$ $elegans$.

In other embodiments, the present invention demonstrates that SA administration deceases formation of IsoK-lysyl-lactam protein adducts. The mechanism by which IsoKs inactivate protein targets involves covalent adduction of the epsilon amine group on the side chains of lysine residues within target proteins (FIG. 2A). The initial product of this covalent adduction is a lactam ring structure composed of the lysyl side chain and the isoketal. SA's amine group is much more reactive toward IsoKs and preserves protein function by more rapidly forming an adduct with the IsoK, preventing the adduction of lysyl side chains. If this mechanism is operative in vivo when $C.$ $elegans$ are treated with SA, a dose-dependent reduction in IsoK-lysyl-lactam adducts should be observed. To test this directly, WT N2 worms were treated with vehicle or increasing concentrations of SA until day 15, then collected for IsoK-lysyl-lactam adduct quantification by liquid chromatography tandem mass spectrometry (LC/MS/MS) using a heavy isotope-labeled internal standard for quantification [56]. SA treatment resulted in a significant, dose-dependent reduction in IsoK-lysyl-lactam adduct levels compared with vehicle control in WT animals ($p<0.01$) (FIG. 2B).

The present invention also demonstrates that SIR-2.1 is a critical protein whose function is preserved by salicylamine. Though SA treatment should prevent IsoK adduct formation on many different protein targets, and many of these proteins could have some impact on lifespan and healthspan, the present inventors determined that there would be specific proteins of particular importance in mediating SA's beneficial effects. Specifically, the present inventors recognized that SIR-2.1 would be one of these "high value targets" for several reasons. Increased activity of SIR-2.1 and its orthologs have been significantly associated with increased lifespan in multiple studies. Sirtuins are lysine deacetylases that are normally found in membrane-bound and membrane-rich subcellular compartments (e.g., mitochondria), so they are in very close proximity to the membrane lipids that give rise to IsoKs and to the lysyl residues that are their targets. Finally, some sirtuin isoforms have been shown to have greatest deacylase activity toward longer acyl chain lysyl moieties, raising the possibility of an enhanced likelihood of SIR-2.1 being present in close proximity to IsoKs and protein lysyl side chains [57, 58]. First, the present inventors wanted to show that isoketals are chemically capable of inactivating sirtuin proteins, as this would lend plausibility to a direct interaction in vivo and would support the inventors' understanding that sufficient oxidative stress, rather than activating sirtuins [42, 59-62], will actually lead to inhibition. Recombinant human SIRT1 was incubated with increasing concentrations of synthetically pure IsoK, and enzymatic deacetylase activity was assessed using the luminescence based Sirt-Glo assay (Promega). Purified isoketals dose-dependently inhibited recombinant human sirtuin 1 (FIG. 3A), with an $IC_{50}$ of 97.8 μM.

Next the present inventors showed that, in vivo, SIR-2.1 is a critical protein that is functionally preserved from time-dependent oxidative inactivation when $C.$ $elegans$ are treated with increasing doses of SA. A nematode strain carrying a non-functional SIR-2.1 mutation, VC199 [sir-2.1 (ok434)] was treated with the same concentrations of SA as were used in lifespan experiments with WT nematodes. Starting at day 1 of adulthood, SIR-2.1 mutants were grown on SA-coated OP50-seeded NGM plates. SIR-2.1 mutant worms were transferred to freshly made SA-OP50-NGM agar plates every 2 days and survival was assessed using a platinum wire until all worms died; survival was scored as movement upon slight touch with the platinum wire (FIG. 3B). When SA was administered to the VC199 strain, the effect of extending median lifespan that had been observed in the N2 strain was entirely abolished (FIG. 3C; VC199 median lifespan: 16 days, 0 µM SA; 15 days, 50 µM SA; 15 days, 100 µM SA; 15 days, 500 µM SA; p=0.70). This shows that SA-mediated lifespan extension acts in part through preservation of sirtuin activity.

The present inventors also show that SIR-2.1 is required for the healthspan extending effects of SA in addition to the longevity effects. As with the N2 strain, the present inventors treated VC199 nematodes with increasing concentrations of SA and assessed the age-dependent accumulation of autofluorescent lipofuscin granules and decrease in pharyngeal pumping rate. In worms lacking SIR-2.1, none of the doses of SA used were able to decrease the accumulation of lipofuscin (FIG. 3D) (p=0.50) or to preserve pharyngeal pumping rates (FIG. 3E) (p=0.50) at day 15. Taken together, these data strongly suggest that SIR-2.1 is a critical target for SA's effects on healthspan as well as lifespan in adult *C. elegans*.

The present inventors also show that SIR-2.1 preservation enhances resistance to oxidant stress but does not affect mitochondrial function. One of the major stimuli for activation of sirtuins is oxidative stress. Multiple sirtuin isoforms in multiple different species have been shown to play an important role in cellular defenses against oxidant injury [42, 61, 62]. Indeed, the mitochondrial antioxidant manganese superoxide dismutase (MnSOD) has been identified as one of the major protein targets that is deacetylated by sirtuin isoforms, with deacetylation enhancing the enzymatic activity of MnSOD [60]. If SA indeed preserves SIR-2.1 enzymatic function in vivo, the present inventors hypothesized that SA treatment would dose-dependently decrease biomarkers of oxidant injury in a SIR-2.1-dependent manner. To quantify oxidant injury, the present inventors measured $F_3$-isoprostanes (F3-IsoPs). F3-IsoPs are the products of free radical-mediated peroxidation of eicosapentaenoic acid (EPA), and are known to be a highly sensitive and accurate marker of oxidative damage in *Caenorhabditis elegans* [63-65]. $F_3$—IsoPs were collected from WT N2 and from VC199 (SIR-2.1 deficient strain) nematodes grown on OP50-NGM agar plates containing increasing concentrations of SA from Day 1 of adulthood until collection at Day 15. Quantification of $F_3$-IsoPs from WT N2 worms (FIG. 4A) exhibited a dose-dependent decrease in $F_3$-IsoP levels, with 100 µM SA decreasing $F_3$-IsoP production by 29% (p<0.01) and 500 µM displaying a 44% decrease in $F_3$-IsoP levels (p<0.005). In sharp contrast, SIR-2.1 deficient nematodes showed a slightly higher baseline level of F3-IsoPs that did not significantly decrease at any dose of SA tested (FIG. 4B), confirming that SA itself does not act as a direct antioxidant and supporting the hypothesis that SIR-2.1 enzymatic activity is preserved by SA treatment with the predicted positive effect on cellular defense against oxidant injury. To further characterize SA's ability to preserve SIR-2.1 function, the present inventors assessed acetylation of MnSOD at Lys 122. At the highest dose of SA (500 µM) on day 15 of adult life, WT N2 nematodes show a trend toward lower acetyl-Lys 122 in MnSOD compared to the VC199 strain treated with the same SA dose (FIGS. 4C and 4D), supporting at least a modest positive effect of SA treatment on MnSOD acetylation state and function, mediated by SIR-2.1.

Mitochondria lie at the center of aging biology, playing crucial roles in energy production, carbon substrate metabolism, apoptosis regulation, and redox balance and signaling [66-68]. Since sirtuins play a major role in regulating mitochondrial function, the present inventors next wanted to investigate whether SA was exerting any of its effects via protection of mitochondrial processes. To investigate SA's effects on mitochondrial respiration, the present inventors administered SA to WT N2 (FIG. 5A) and non-functional SIR-2.1 mutant worms (FIG. 5B) and measured oxygen consumption rate (OCR) in whole worms over several days. OCR decreased with age in both N2 and VC199 strains, and SA showed no effect on mitochondrial OCR in either strain (p>0.05). The present inventors also examined the effect of SA treatment on mitochondrial DNA (mtDNA) integrity. Using a quantitative polymerase chain reaction (qPCR) assay to measure mtDNA content relative to nuclear DNA, WT N2 (FIG. 5C) and VC199 SIR-2.1 mutants (FIG. 5D) showed no significant difference in mtDNA copy number with age or with SA treatment. Taken together, these data suggest that the SIR-2.1 dependent effects of SA treatment are not mediated through significant changes in mitochondrial function.

The present inventors also discovered that gene expression analysis reveals ets-7 as an important effector of salicylamine. Programmed aging is one of the major theories of aging, wherein this theory implies there is a built-in program in the genome that activates senescence, which leads to death [69]. In addition to the functions discussed above, sirtuins can have powerful regulatory effects on gene expression programs by virtue of their proposed histone deacetylase activity. With supporting evidence that SA's effects are at least in part SIR-2.1 mediated, the present inventors sought to better define the role of changes in global gene expression following SA treatment in WT N2 worms. The present inventors understood that there would be fairly broad changes in gene expression that would converge on one or more specific pathways. To assess whether SA alters an aging gene transcriptional program, the present inventors carried out microarray analysis on adult WT N2 worms exposed to SA (0, 100, 500 µM SA) for 15 days. Gene expression arrays showed that, surprisingly, SA treatment exerted a relatively minor effect on gene expression, with the major variable impacting on gene expression being aging itself. From the microarray, the present inventors identified 26 genes upregulated by both 100 and 500 µM SA (Group I), 38 genes more strongly downregulated by 500 µM SA than 100 µM SA (Group II), 15 genes with variable downregulation (Group III), and 30 genes downregulated by both doses of SA (Group IV) (FIG. 6A). Of the 8,902 probe sets with unigene identifiers, only 109 probe sets showed at least a 25% change in expression with SA administration at Day 15. Thus, the major effect of SA treatment appears to be at the post-translational level, as would be predicted by SA's proposed mechanism of action.

Nonetheless, there were some significantly changed genes downstream from SA treatment. First, to validate the microarray results, the present inventors performed real-time RT-PCR on four genes, siah-1, sma-4, F13D12.6, and ets-7 (FIG. 6B). The genes, siah-1 and sma-4 showed downregulation by SA in Day 15 WT N2 worms, and F13D12.6 and ets-7 showed upregulation by SA. Messenger RNA levels for siah-1 and sma-4 were decreased by nearly 25%, as well as F13D12.6 and ets-7 were increased by nearly 25% by SA administration (p<0.05). Pathway Analysis using Gene Ontology (GO) with WEB-based Gene SeT Analysis Toolkit (WEBGESTALT <http://bioinfo.vanderbilt.edu/webgestalt/>) highlighted the metabolic process, lipid metabolic process, proteolysis pathways among many others as being altered favorably by the administration of SA (see Supplemental Data). From the array data confirmed by RT-PCR, the present inventors identified the ETS class transcription factor ETS-7 as a protein of interest. ETS factors are known to be involved in regulating lipid metabolism and regulate lifespan in both Drosophila melanogaster and C. elegans [70, 71]. To investigate the role of ETS-7 in regulating lifespan downstream from salicylamine, SA was administered to the ets-7 gene knock-out strain, RB981 [F19F10.5(ok888) V]). Similar to the SIR-2.1 deficient VC199 strain, loss of ets-7 showed no SA-mediated effect on lifespan extension (RB981 median lifespan: 16 days, 0 µM SA; 15 days, 500 µM SA, p>0.05) (FIGS. 6C and 6D). The present inventors originally hypothesized that upregulation of ets-7 depends on SIR-2.1, which could result in enhanced longevity. In order to test this, the present inventors carried out real-time RT-PCR quantification of ets-7 in non-functional SIR-2.1 mutant nematodes treated with increasing doses of SA (FIG. 6E). Messenger RNA levels for ets-7 were increased by 32% in Day 15 WT N2 worms by 500 µM SA administration (p<0.05), and similarly, a dose-dependent increase in ets-7 transcriptional level can be observed in Day 15 non-functional SIR-2.1 mutants, VC199, with the highest dose of SA showing a significant 442% increase in mRNA expression (p<0.01). Taken together, these findings suggest that ets-7 upregulation in non-functional SIR-2.1 mutant is an attempt at compensation for loss of SIR-2.1, which is further enhanced by SA-administration, but ultimately insufficient in attenuating longevity in the absence of SIR-2.1. Our data suggest that ets-7 is necessary for SA-dependent increase in lifespan, but is insufficient without the presence of functional SIR-2.1.

In embodiments of the present invention, the present inventors have shown that treatment with salicylamine, a scavenger of some of the most damaging products of oxidant injury—namely, γ-ketoaldehydes generally, and isoketals specifically—can prolong natural lifespan and healthspan in C. elegans, and that these effects are dependent upon SIR-2.1 and ETS-7. Embodiments of the present invention have shown that the effects of SA operate primarily at the protein level, in keeping with what is known about the biochemical mechanism of action and placing SA broadly in the role of a proteostasis mediator. The present inventors further show that, although SIR-2.1 and ETS-7 are important targets preserved by SA treatment, the major biochemical effect of preserving the activities of these two targets is to enhance normal antioxidant defenses, with effects on mitochondrial function, mtDNA integrity, and gene expression being small to nonexistent.

Several aspects of the inventor's work are worth particular attention. First, SA treatment was begun and exhibited its effects in adult worms. This is distinct from some other longevity-extending interventions which rely on genetic manipulation or application of a particular treatment or stressor during a critical developmental period [72-75]. Such interventions are certainly informative but are likely to be of limited direct translation potential. Second, though SA exhibited predictable effects on oxidative stress by way of SIR-2.1 mediated activation of antioxidant enzymes (e.g., MnSOD), the lack of effect on gene expression and on mitochondrial function was striking and informative. This suggests that SA is not working through maintenance or modification of large gene expression programs, nor probably through maintenance of overall nuclear and/or mitochondrial genomic integrity, nor through large effects on mitochondrial function. The lack of any apparent effect on mitochondrial oxygen consumption is perhaps a bit surprising, given the central role of SIR-2.1 in mediating the effects of SA treatment. However, SIR-2.1 is known to exert a wide range of pleiotropic effects beyond metabolic regulation [45, 49, 76-78], and our data would be consistent with preservation of any number of these other functions ascribed to SIR-2.1. Finally, SA treatment does not appear to induce any of the stress/hormesis loops [34, 75, 79, 80] that have been shown to impact upon longevity when activated or inhibited.

The identification of ETS-7 by gene expression array and the subsequent finding that ETS-7 is necessary but not sufficient for SA to exert its effects deserves specific mention. The present inventors focused on ETS-7 particularly because there is precedent in the literature for ETS family transcription factors regulating longevity through effects on lipid metabolism [70, 71, 81]. Given that other lipid metabolic genes were shown to be significantly regulated by SA treatment, the present inventors reasoned that ETS-7 may be an important regulatory gene, with the other lipid metabolism genes identified being downstream from ETS-7. The finding that ETS-7 is required for SA's effects, but DAF-16 is not, suggests that there are indeed specific protein targets modulated by SA. Furthermore, the observed interactions between SA, SIR-2.1, and ETS-7 strongly suggest that extension of natural lifespan by SA treatment occurs through preservation of the biochemical activities of multiple regulatory proteins, with SIR-2.1 serving as a primary node in the signaling pathway and ETS-7 playing a secondary role. Further delineation of all of the important signaling nodes impacted by SA treatment and elucidation of the signaling hierarchy will be major areas of focus for future investigations.

The translation potential for compounds of the present invention as a clinically useful anti-aging therapy is high. Salicylamine is orally bioavailable in mammals [21]. Long-term administration (approximately one year) in mice via drinking water has shown no evidence of intolerance and no evidence of excess adverse events [22]. This is particularly important when considering an anti-aging intervention, as the present inventors would anticipate that SA would need to be administered on an ongoing basis over a long period of time given its mechanism of action. No excess tumor formation was observed in mice with long-term SA treatment [82-84], an important negative given recent reports regarding negative effects of nonspecific antioxidant therapies with regard to tumor metastasis [85, 86]. Finally, the translation of SA into human studies should be able to proceed fairly rapidly, as it is a naturally occurring small molecule found in buckwheat seeds and is currently awaiting FDA Generally Recognized as Safe (GRAS) designation for use as a natural supplement.

EXAMPLES AND METHODS

C. elegans Strains and Maintenance

C. elegans strains were cultured at 20° C. on standard nematode growth media (NGM) agar plates seeded with Escherichia coli strain NA22. The following strains were used in this work: wild-type C. elegans Bristol strain (N2), sir-2.1(ok434) IV, F19F10.5(ok888) V, and daf-16(mu86). Strains were obtained from the Caenorhabditis Genetics Center (University of Minnesota, St. Paul, Minn.). For generating cultures of 15-day-old (Day 15) adult worms, synchronized late-stage L4s/early young adult worms [87] were transferred to peptone enriched 15 cm plates containing UV-irradiated OP50 E. coli and 0.12 mM 5-fluoro-2'- deoxyuridine (FUDR) to inhibit progeny production[88] with or without drug until harvest.

Salicylamine Exposure

Nematodes grown on NGM-agar plates containing 0.5% peptone, were harvested, and eggs were isolated by alkaline hypochlorite with 0.5 N NaOH, 1% hypochlorite; 8 min at 23° C. The recovered eggs were rinsed in M9 buffer and placed on fresh agar plates seeded with E. coli strain OP50 and maintained at 20° C. until late-L4/young adult stage. After the late L4/young adult molt, worms were transferred to peptone enriched 15 cm plates containing 0.12 mM FUDR, OP50 E. coli, and varying concentrations of SA. Salicylamine drug plates were made fresh before transfer by spreading SA on top of the agar and plates were allowed to dry. E. coli strain OP50 was exposed to UV radiation for 30 minutes to kill the bacteria before seeding onto the SA-FUDR NGM agar plates. Worms were exposed to SA throughout its life until harvest by transferring worms to fresh SA-FUDR-OP50 NGM plates every other day.

Longevity Assays

Survival cultures were grown on 60-mm agar plates; after the late-stage L4/young adult molt, approximately 100 adults were transferred onto SA-OP50-seeded NGM plates. Salicylamine drug plates were made fresh before transfer by spreading SA on top of the agar. Plates were allowed to dry before seeding with UV-irradiated OP50 bacteria. Worms were maintained at 20° C. and live worms were counted during transfer to freshly made SA-OP50-NGM agar plates every 2-3 days. Survival was scored as movement upon slight touch with the platinum wire. Worms were maintained until death.

Autofluorescence Measurement

Synchronized late L4/early young adult worms were plated on FUDR containing SA-OP50-seeded NGM plates and worms were maintained at 20° C. Every fifth day, 10-15 worms were mounted onto 2% agar pads and anesthetized with 3 mM levamisole in DMSO. Images were taken at 250-ms exposure under a DAPI filter using an epifluorescence microscope (Nikon Eclipse 80i) equipped with a Lambda LS Xenon lamp (Sutter Instrument Company) and Nikon Plan Fluor 20× dry and Nikon Plan Apo 60×1.3 oil objectives. The fluorescence was calculated using ImageJ software[89].

Pharyngeal Pumping

C. elegans pharyngeal pumping rate assays were performed on 60-mm agar plates with bacterial lawns at room temperature. Every fifth day, worms were transferred to fresh bacteria-seeded NGM plates, and incubated at 25° C. for 10 min in order to equilibrate feeding rates before measurement. After 10 min incubation, worms were observed under the Zeiss TLB 3.1 microscope with focus on the pharynx. The number of contractions in the terminal bulb of the pharynx was counted for 20 s and then plotted.

Oxygen Consumption Analysis

Oxygen consumption rate for whole C. elegans was measured using a Seahorse Bioscience XF$^e$96 Analyzer. Worms were harvested from Day 0, 2, and 15 colonies maintained on FUDR containing SA-OP50-seeded NGM plates by washing in M9 medium, followed by floatation on an ice-cold 60% w/v sucrose gradient to segregate clean bacteria-free adult worms from bacterial debris. Worms were seeded at 1,000 worms/well in M9. After 20 min equilibration, a 2-min measurement was performed to obtain basal OCR for all experimental conditions and strains.

Genome Copy Number Analysis

Relative mitochondrial and nuclear copy number were measured by quantitative, real-time PCR [90]. Primers for NADH dehydrogenase unit 1 (nd1) and a 164 bp region of the cox-4 gene were used in determination of mtDNA copy number. The nd1 forward primer 5'-AGCGTCATTTAT-TGGGAAGAAGAC-3' and reverse 5'-AAGCTTGTGCTAATCCCATAAATGT-3'. Cox-4 forward primer 5'-GCC GAC TGG AAG AAC TTG TC-3' and reverse primer 5'-GCGGAGATCACCTTCCAGTA-3'. Real-time PCR conditions were 2 min at 50° C., 10 min at 95° C., followed by 40 cycles of 15 s at 95° C., and 60 s at 63° C. Amplified products were detected with SYBR Green (iQ™ SYBR® Green Supermix, Bio-Rad) and fluorescent signal intensities were determined by CFX96 Touch™ Real-Time PCR Detection System (Bio-Rad) by software CFX Manager™ (version 3.1). Crude worm lysate was harvested from Day 0, 2, and 15 stage nematodes grown on FUDR containing SA-OP50-seeded NGM plates and used as template DNA for real-time PCR based determination of mtDNA and nucDNA copy numbers.

NAD+-Dependent Deacetylation in Bioluminescence Assay

Relative activity of the NAD+-dependent histone deacetylase (HDAC) class III enzymes (sirtuins) was measured using the SIRT-Glo™ Assay and Screening System (Promega Corporation, Madison, Wis.) according to the manufacturer's instructions with minor modifications. This assay uses an acetylated, luminogenic peptide substrate that can be deacetylated by SIRT activities. Deacetylation of the peptide substrate is measured using a coupled enzymatic system with a protease in the reagent provided and then cleaves the luminogenic peptide to liberate aminoluciferin. Free aminoluciferin can be quantified using the Ultra-Glo™ firefly luciferase reaction to produce a stable, persistent emission of light. Purified recombinant human SIRT1 (R&D Systems, Biotechne) activity was assayed in HEPES-buffered saline (10 mM HEPES, 150 nM NaCl, 2 mM $MgCl_2$) in the presence and absence of 15-$E_2$-IsoK. 15-$E_2$-IsoK was synthesized by the method of Armanath et al [91]. Luminescence was detected by a microplate reader (FLUOstar Optima microplate reader, BMG Labtechnologies).

Sample Preparation and Detection of Endogenous $F_3$-IsoPs by GC/MS $F_3$-Isoprostanes were quantified from SA-treated worms a gas-chromatography-negative ion chemical ionization-mass spectrometry (GC-NICI-MS) approach [92]. Worms maintained on FUDR containing SA-OP50-seeded NGM plates were harvested at Day 15 by washing in M9 medium, followed by floatation on an ice-cold 60% w/v sucrose gradient to segregate clean bacteria-free adult worms from bacterial debris. Clean worms were transferred to Eppendorf tubes and homogenized using the Mini-Beadbeater-24® (BioSpec, Bartlesville, Okla.) with zirconium oxide beads (1.0 mm), at 4° C. Homogenates were then hydrolyzed by 15% w/v KOH, containing 57 µM BHT (5% w/v BHT:MeOH) for 30 min at 37° C. Next, samples were centrifuged at max speed to pellet worm debris and supernatant was transferred to a 16-mL polypropylene tubes (Denville Scientific, Inc., Holliston, Mass.).

Samples were spiked with 248 pg of deuterated internal standards, $[^2H_4]$-15-$F_{2t}$-IsoP, quantified and calibrated by the method of Milne et al. [92] and acidified to pH<3 with HCl in preparation for further Separation Phase Extraction (SPE). $C_{18}$ Sep-Pak cartridges (Waters, Milford, Mass.) were preconditioned with 5 mL of MeOH, followed by 5 mL of pH 3 water and subjected to vacuum to obtain a flow rate of 1 mL/min. Samples were applied to the cartridges and allowed to flow through completely before adding equal volume of pH 3 water and heptane to wash columns before eluting with ethyl acetate:heptane (1:1 v:v). Anhydrous sodium sulfate was then added to each sample to absorb excess water from samples and then applied to silica Sep-Pak cartridges (Waters, Milford, Mass.) preconditioned with ethyl acetate. Samples were transferred to the silica Sep-Pak columns and allowed to pass through before washing with ethyl acetate, and eluted with ethyl acetate:MeOH (45:55 v:v).

Eluates were dried under nitrogen and $F_3$—IsoPs and resuspended in MeOH for separation by Thin Layer Chromatography (TLC). The free acid TLC standard, 8-iso-Prostaglandin $F_{2\alpha}$ methyl ester (8-iso-PGF$_{2\alpha}$, Cayman Chemicals, Ann Arbor, Mich.) and samples were spotted on pre-washed silica TLC plates, placed in a TLC tank containing chloroform:MeOH:Acetic acid (84.5:14.5:1 v:v:v), and allowed to run until reaching solvent front. The free acid TLC standard was visualized by spraying standard plate with phosphomolybdic acid solution, and samples were scraped from the TLC plate in the region of the TLC standard ($R_f$~0.35). Samples were extracted from silica by resuspension in ethyl acetate:EtOH (1:1 v:v) and dried under nitrogen. All steps from this point followed the $F_3$-IsoP measurement protocol as described by the method of Nguyen et. al. [63]. Deuterated $F_2$-IsoP standard was measured at m/z 573. $F_3$—IsoP was measured at m/z 567. Endogenous $F_3$-IsoP levels were quantified by comparing the height of the peak containing the derivatized $F_3$-IsoP to the height of the deuterated internal standard peak.

Protein concentration of nematode homogenates were determined using the bicinchoninic acid (BCA) protein assay as described by the manufacturer (Pierce Protein Biology, Waltham, Mass.).

Quantification of Isoketal Protein Adducts Using LC/MS

Worms grown on FUDR containing SA-OP50-seeded NGM plates were collected at Day 15 adult stage by washing in M9 medium, followed by an ice-cold 60% w/v sucrose gradient to segregate clean bacteria-free adult worms from bacterial debris. Clean worms were transferred to Eppendorf tubes and flash-frozen in liquid nitrogen and thawed at 37° C. 3×. Samples were homogenized using a handheld homogenizer (Polytron PT 1200E, KINEMATICA AG), in buffer containing antioxidants (100 μM indomethacin, 220 μM butylated hydroxytoluene, and 5 mM triphenylphosphine) and 100 μM pyridoxamine dihydrochloride to prevent artifactural generation of IsoK protein adducts during sample processing. Levels of IsoK-lysyl-lactam adduct was measured as previously described [56].

In brief, IsoK protein adducts are measured after enzymatic proteolysis and separation as IsoK-lysyl-lactam adducts by liquid chromatography tandem mass spectrometry (LC/MS/MS) using a heavy isotope labeled internal standard for quantification. Samples were treated with 15% KOH to hydrolyze esterified isoketals and then subjected to complete proteolytic digestion using pronase protease (*Streptomyces griseus*, Calbiochem, San Diego, Calif.) and aminopeptidase M (Calbiochem, San Diego, Calif.), consecutively, to release the IsoK-lysyl-lactam adduct. After digestion, 500 pg of a ($^{13}C_6$)-IsoK-lysyl-lactam internal standard was added to each sample, followed by partial purification of lysyl adducts by solid-phase extraction (SPE) and further purification by preparative HPLC (2690 Alliance HPLC system, Waters, Milford, Mass.). Isok-lysyl-lactam adducts were then quantified by selective reaction monitoring LC electrospray tandem mass spectrometry for transition from m/z 479→84 and m/z 487→90 for internal standard (ThermoFinnigan Surveyer MS pump coupled to TSQ quantum triple-quadrupole mass spectrometer, Thermo Fischer Scientific, Waltham, Mass.).

Protein concentration of nematode homogenates were determined using the Thermo Scientific Pierce BCA Protein Assay as described by the manufacturer (Pierce Protein Biology, Waltham, Mass.).

Western Blot

Day 15 adult worms grown on FUDR containing SA-OP50-seeded NGM plates were harvested in M9 medium, followed by floatation on an ice-cold 60% w/v sucrose gradient to segregate clean bacteria-free adult worms from bacterial debris. Clean worms were transferred to Eppendorf tubes containing radioimmunoprecipitation assay (RIPA) buffer with protease inhibitor, trichostatin A, nicotinamide, and phosphatase inhibitors and flash-frozen in liquid nitrogen and thawed at 37° C. 3×. Twenty to thirty μg of protein were loaded onto a 10% SDS-PAGE acrylamide gel. Proteins were electroblotted onto nitrocellulose membranes, blocked with 0.1% Tween PBS with 5% nonfat milk and 0.05% sodium azide, and western blots were performed with the primary antibodies anti-MnSOD (ab13533, AbCam, Cambridge, Mass.), anti-acetyl-lysine 122 MnSOD (a generous gift of D. R. Gius, Northwestern University at Chicago, Ill., USA; Epitomics, Inc, Burlingame, Calif.), anti-acetyl-lysine 68 MnSOD (a generous gift of D. R. Gius, Northwestern University at Chicago, Ill., USA; Epitomics, Inc, Burlingame, Calif.), and anti-β-actin (A5316, Sigma, St. Louis, Mo.). Proteins were visualized by species-appropriate secondary antibodies labeled with horseradish peroxidase (Santa Cruz Biotechnology, Dallas, Tex.) and chemiluminescent substrate (Amersham ECL Prime Western Blotting Detection Reagent, GE Healthcare, Pittsburgh, Pa.). Densitometry was obtained with ImageJ.

Microarray Analyses

Total RNA was isolated via the Trizol method. Worms maintained on FUDR containing SA-OP50-seeded NGM plates were harvested at Day 15 by washing in M9 medium, followed by floatation on an ice-cold 60% w/v sucrose gradient to segregate clean bacteria-free adult worms from bacterial debris. Clean worms were transferred to Eppendorf tubes containing Trizol (Life Technologies) and then snap-frozen in liquid nitrogen and thawed at 37° C. 3×. Chloroform was added to each sample, followed by precipitation using isopropanol and washing with 75% ethanol. The supernatant was then transferred to an RNeasy MinElute (Qiagen Inc., Valencia, Calif.) spin column and all steps from this point followed the RNA purification protocols described in the manufacturer's instructions.

This mixture was then vortexed and transferred to a Shredder Column (Qiagen Inc., Valencia, Calif.) and centrifuged. Eluate from the Shredder Column was transferred to a Preclear Column contained in the Versagene Kit and all steps following protocols described in the kit manual. After isolation, total RNA was reverse transcribed to double-stranded cDNA, amplified, labeled, and fragmented using the NuGEN Ovulation Biotin Kit (San Carlos, Calif.). Fragmentation was confirmed using an Agilent Bioanazlyer 2100 (Santa Clara, Calif.) and fragmented, labeled product was hybridized to an Affymetrix *C. elegans* Gene 1.0 ST GeneChip (Santa Clara, Calif.) according to the manufacturer's protocols.

Microarray data analysis was performed on arrays normalized by Robust Multi-chip Analysis (RMA). The quality controls on samples and on probe sets were performed stepwise to detect the outlying samples and poor probe sets. The Principal Components Analysis (PCA) score plot and hybridization controls plot were applied for sample detection, with at least one sample with log 2(expression)>7. Filtering for high-quality data resulted in 109 genes with at least 25% change in expression, which were defined as salicylamine responsive genes. Independent validation of microarray results was performed by examining changes in mRNA expression using RT-PCR methods as described below.

TaqMan Gene Expression Assay

Total RNA was isolated via the Trizol method, as described previously. Following isolation, 2 μg total RNA was used for cDNA synthesis using the High Capacity cDNA Reverse Transcription Kit (Life Technologies), per manufacturer's instructions. Quantitative real time PCR (Bio-Rad) was conducted using TaqMan Gene Expression Assay Probes (Life Technologies) for each gene. Amplified products was normalized to housekeeping gene, ama-1 (RNA polymerase II) after determining fold difference using the comparative $2^{-\Delta\Delta ct}$ method [93]. The following probes were used: ama-1 (Assay ID: Ce2462269_m1), ets-7 (Ce02477624_g1), F13D12.6 (Ce02439540_m1), siah-1 (Assay ID: Ce02462269_m1), and sma-4 (Assay ID: Ce202447346_1).

Statistics

All statistical analyses were performed using GraphPad Prism 6 (GraphPad Software, Inc.). Concentration response curves were generated using a sigmoidal dose-response model with a top constraint at 100%. Statistical significance of the lifespan experiments were assessed using Mantel-Cox log-rank test, a nonparametric measure that assesses differences in entire survival curves. Comparisons between two groups were performed using a two-tailed Student's t-test assuming equal variances. Multiple group comparisons at different time points was done using two-way ANOVA with repeated measures, followed by Bonferroni's multiple comparison post-hoc tests. Values of $P<0.05$ were considered statistically significant.

REFERENCES

Figure 1:
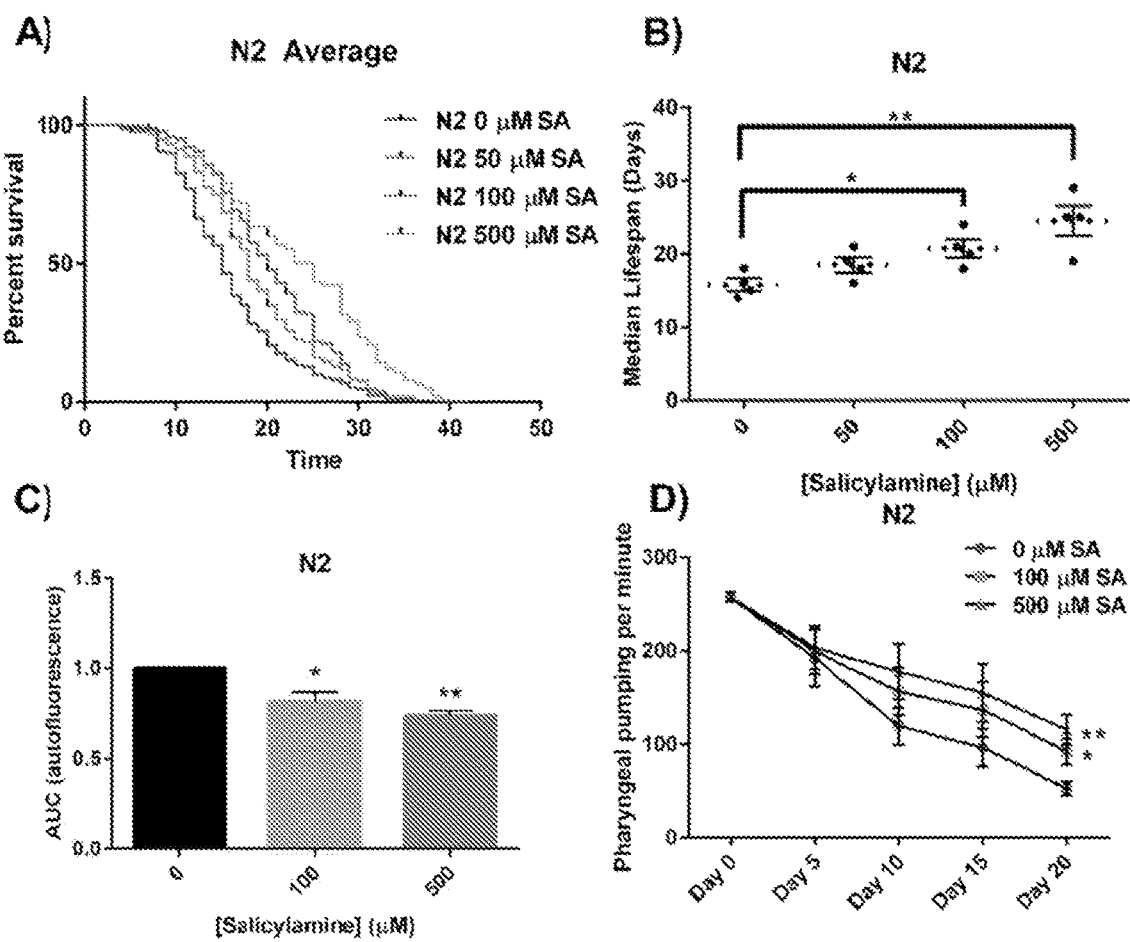
FIG. 1. SA extends the lifespan of N2 C. elegans worms. (A) Kaplan-Meier survival curves for concentration dependency of SA-mediated N2 lifespan extension. Upon day 1 of adulthood, SA was administered every 2 days and survival was assessed every other day until all the worms died. (B) Summary of SA treated N2 median lifespans. SA administration shows a dose-dependent increase in median lifespan. Data are expressed as means±SEM from four independent experiments. *$P<0.05$ as compared with vehicle control, **$P<0.01$ as compared to vehicle control. (C) Effects of SA-mediated decreases in lipofuscin autofluorescence accumulation with age. SA response profiles were generated from integrating the area-under-the-curve (AUC) of fluorescent intensity as a function of time. Compared with N2 vehicle control, treatment with SA shows a significant reduction in autofluorescence. Data are expressed as means±SEM from five independent experiments. *$P<0.01$ as compared with vehicle control, **$P<0.005$ as compared to vehicle control. (D) Changes in pharyngeal pumping rate of aging worms. Pumping rate declines with age, however SA administration retards decline in pumping rate. Data are expressed as means±SEM from five independent experiments. *$P<0.05$ as compared with vehicle control, **$P<0.01$ as compared to vehicle control.
Figure 2:
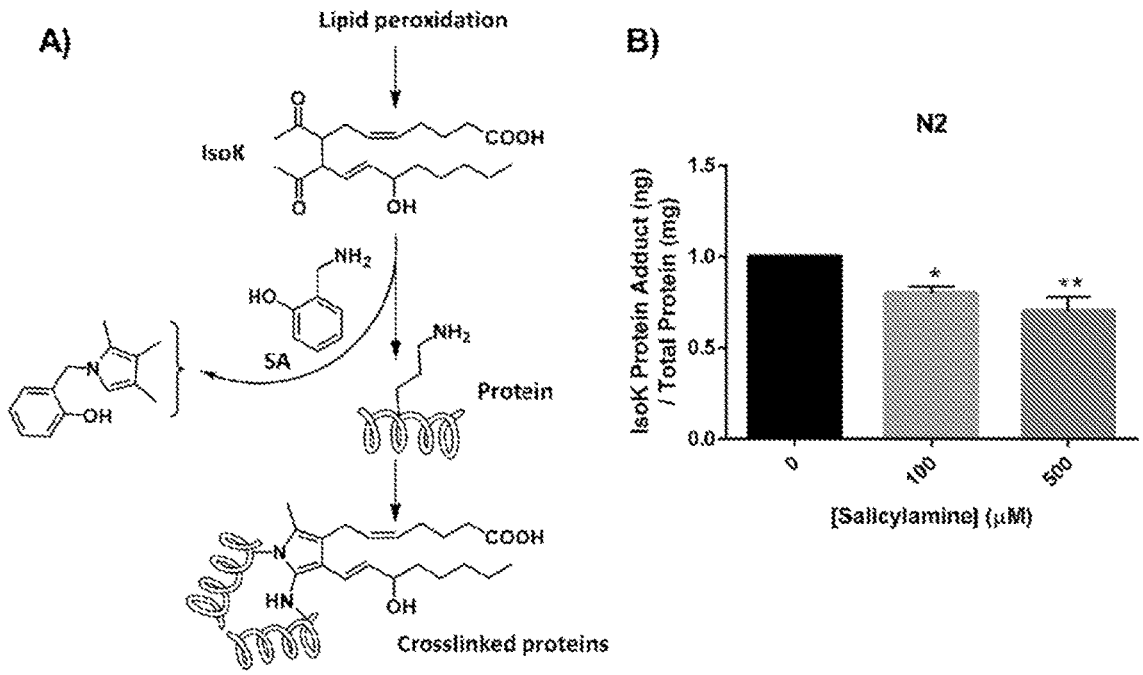
FIG. 2. SA administration decreases formation of IsoK-lysyl-lactam protein adducts. (A) Schematic illustrating lipid peroxidation and formation of IsoKs. Isoks react with ε-amino in lysyl residues of proteins to form stable lactam adducts. Addition of the IsoK scavenger, SA, prevents IsoK adduction. (B) IsoK-lysyl-lactam adduct quantification by LC/MS/MS. IsoK-lysyl-lactam adducts were decreased with SA treatment. Data are expressed as means±SEM from four independent experiments. *$P<0.01$ as compared with vehicle control, **$P<0.005$ as compared to vehicle control.
Figure 3:
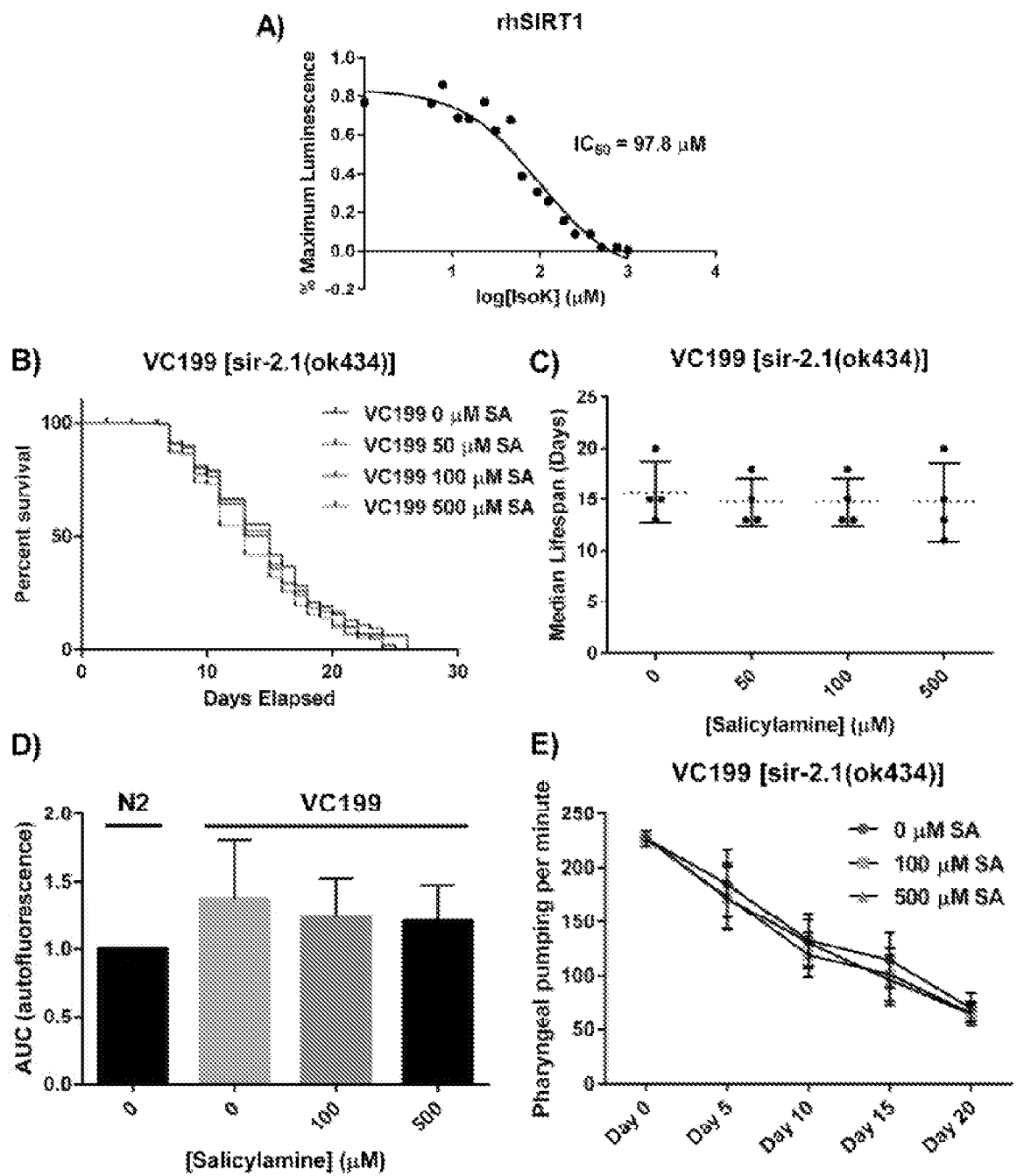
FIG. 3. SIR-2.1 is required for SA-mediated lifespan extension. (A) Synthetically purified IsoKs decrease biochemical activity of rhSIRT1. Recombinant human SIRT1 was incubated with increasing concentrations of IsoK and enzymatic activity was assessed using a luminescence based assay. Concentration-response curves were generated and IC50 values were calculated from three independent experiments. (B) Kaplan-Meier survival curves depicting effects of SA administration on lifespan of non-functional SIR-2.1 mutant. (C) Summary of SA-treated SIR-2.1 mutant median lifespan. SA administration does not affect median lifespan of SIR-2.1 mutants. Data are expressed as means±SEM from four independent experiments. $P=0.70$. (D) Changes in lipofuscin autofluorescence accumulation with age. Compared to vehicle control in WT animals, SA response profiles indicate neither dose of SA were able to decrease the accumulation of lipofuscin. Data are expressed as means±SEM from four independent experiments. $P=0.5$. (E) Changes in pharyngeal pumping rate in SA-treated SIR-2.1 mutants. Administration of SA failed to preserve pharyngeal pumping rate. Data are expressed as means±SEM from four independent experiments. $P=0.5$.
Figure 4:
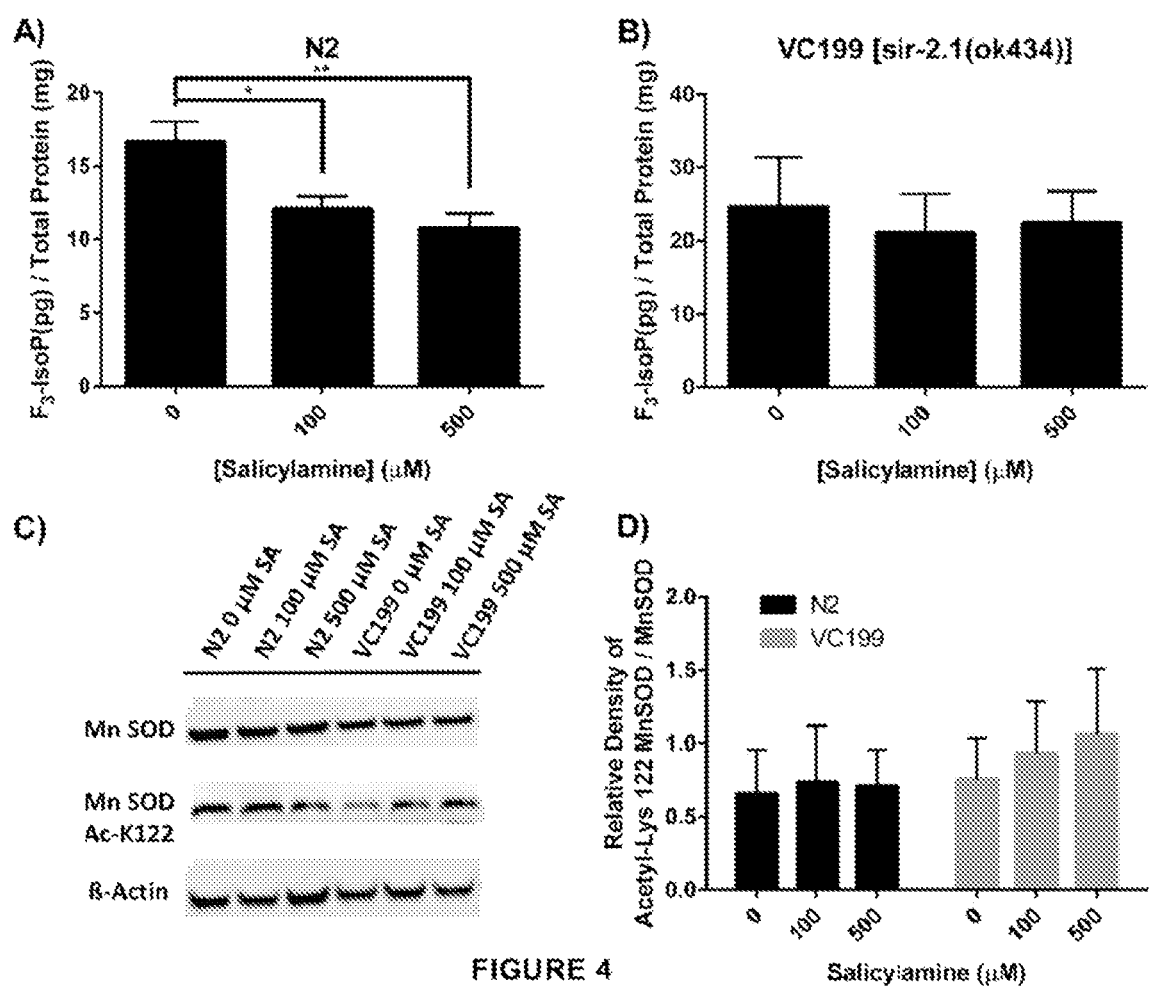
FIG. 4. SA treatment dose-dependently decreases biomarkers of oxidant injury in a SIR-2.1-dependent manner. (A, B) Quantification of oxidant damage via $F_3$-IsoP measurement. N2 WT and SIR-2.1 mutant animals were given SA from day 1 of adulthood until collection. Lysates were collected at day 15 of adulthood and $F_3$—IsoPs were measured by GC/MS. Data are expressed as means±SEM from four independent experiments. *$P<0.01$ as compared with vehicle control, **$P<0.005$ as compared to vehicle control. (C) Levels of acetyl-Lys 122 MnSOD was measured from N2 WT and SIR-2.1 mutant protein extracts and analyzed by Western blot. (D) Quantification of acetyl-Lys 122 MnSOD. Treatment with SA in WT N2 nematodes show a trend toward lower acetyl-Lys 122 MnSOD compared to SIR-2.1 mutant animals. Data are expressed as means±SEM from four independent experiments. $P>0.05$.
Figure 5:
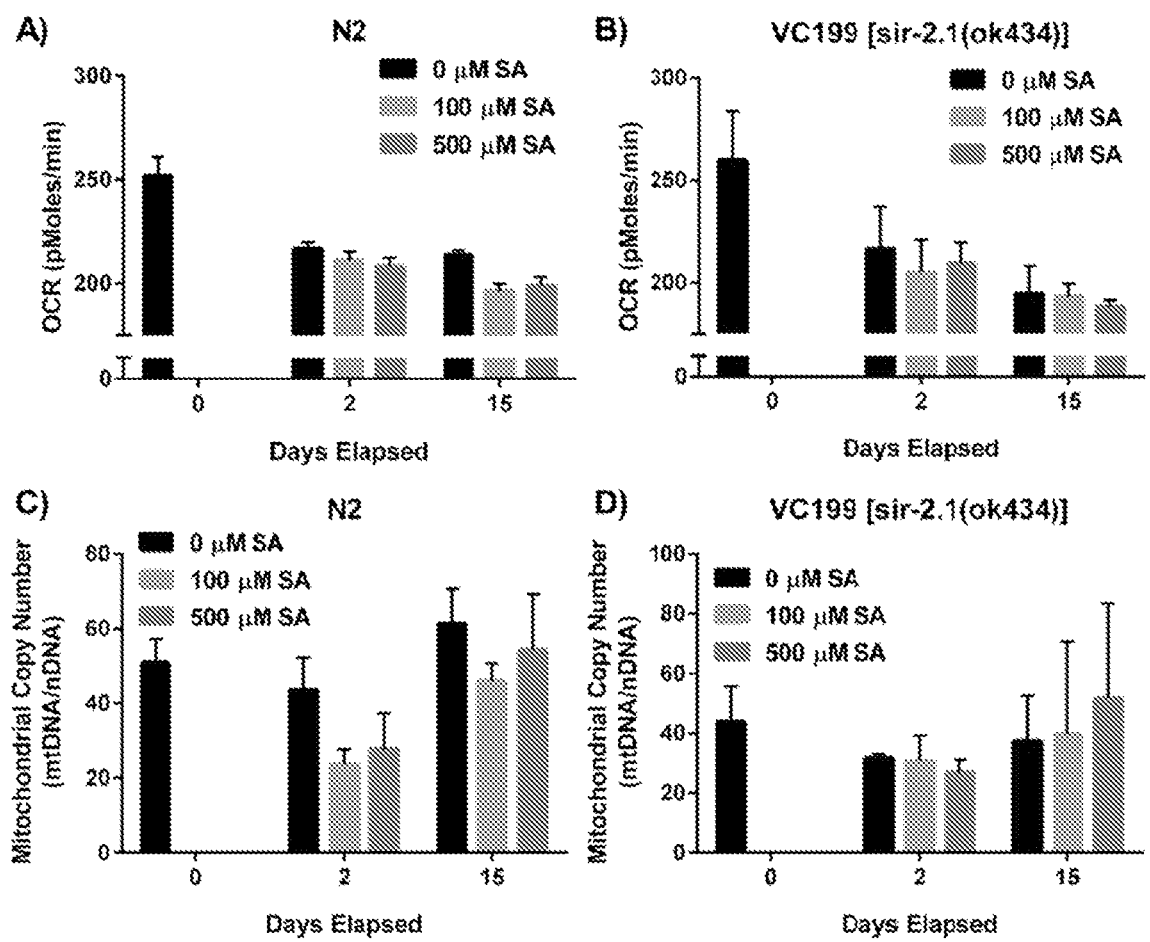
FIG. 5. SIR-2.1 preservation does not affect mitochondrial function. (A, B) SA administration does not alter oxygen consumption rate (OCR). OCR of N2 WT and SIR-2.1 mutation in the presence and absence of SA was measured over time via XF Seahorse Biosciences Analyzer™. Data are expressed as means±SEM from four independent experiments. $P=0.1$ and $P=0.3$, respectively. (C, D) SA treatment does not alter mtDNA integrity. Analysis of mtDNA content collected over time from lysates of SA-treated N2 WT and SIR-2.1 mutant animals. Data are expressed as means±SEM from four independent experiments. $P=0.1$ and $P=0.6$, respectively.
Figure 6:
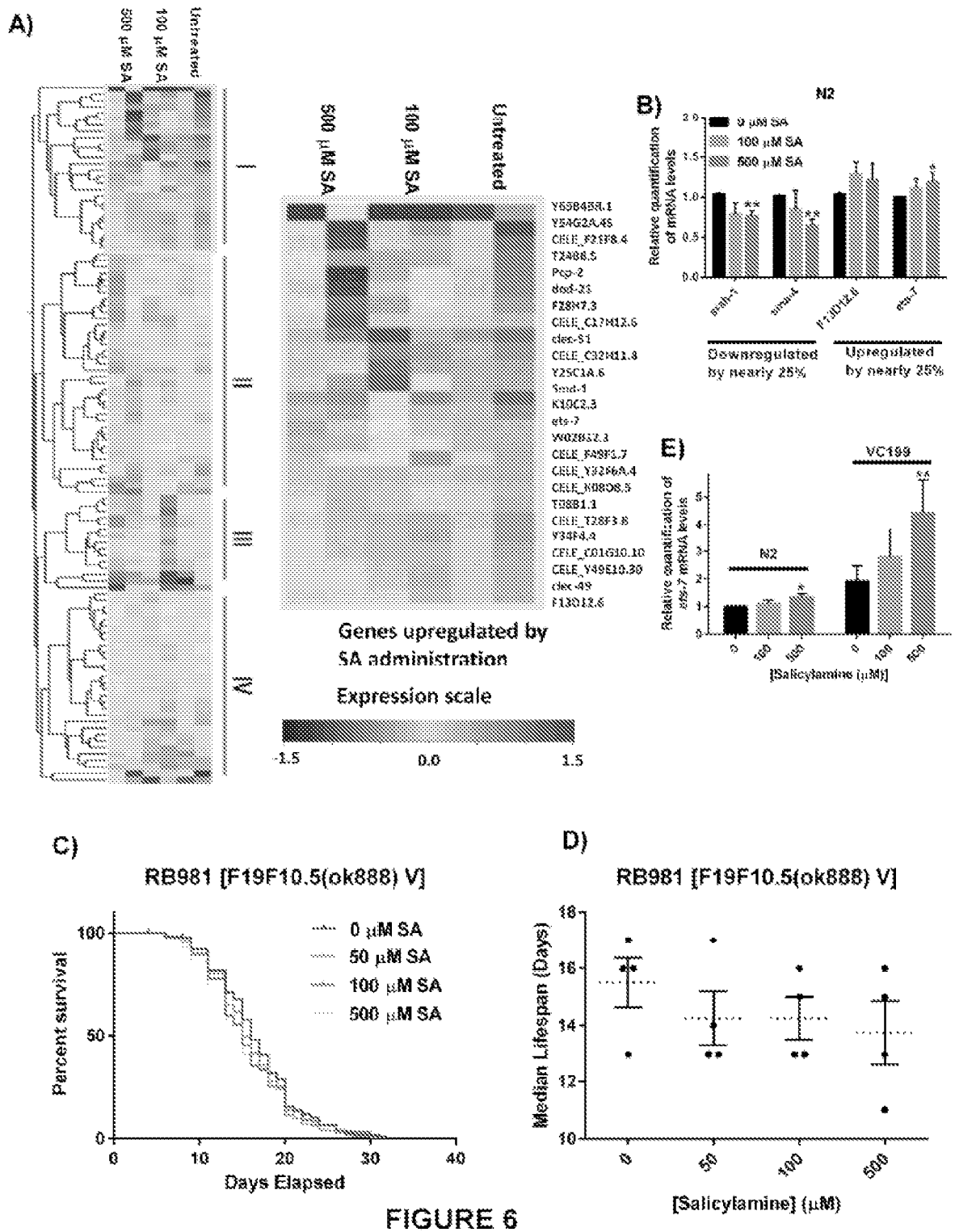
FIG. 6. Gene expression analysis reveals ets-7 as an important effector of SA. (A) Heat map of genes differentially regulated by treatment in 15 day CE. 109 probe sets had at least a 25% change in expression concordant in both samples. These include 26 genes upregulated by both doses of SA (group I), 38 genes more strongly downregulated by 500 μM SA than 100 μM SA (Group II), 15 genes with variable downregulation (Group III), and 30 genes downregulated regardless of dose of SA (Group IV). (B) Real-time RT-PCR validation of microarray results on selected genes. The genes, siah-1 and sma-4 showed downregulation by SA in day 15 WT N2 worms, and F13D12.6 and ets-7 showed upregulation by SA. Data are expressed as means±SEM from five independent experiments. *P<0.05 as compared to vehicle control, **P<0.01 as compared to vehicle control. (C) Kaplan-Meier survival curves for concentration dependency of SA-mediated ets-7 knock-out mutant lifespan extension. (D) Summary of SA-treated ets-7 knock-out mutant median lifespan. SA administration does not affect median lifespan of ets-7 knock-out mutants. Data are expressed as means±SEM from five independent experiments. P=0.40. (E) Real-time RT-PCR quantification of ets-7 in non-functional SIR-2.1 mutant nematodes treated with increasing doses of SA. Transcriptional levels for ets-7 were increased by 25% in day 15 N2 WT worms by SA administration, and a dose-dependent increase in ets-7 mRNA levels can be observed in day 15 SIR-2.1 mutants. Data are expressed as means±SEM from four independent experiments. *P<0.05 as compared to vehicle control, and **P<0.01 as compared to vehicle control.
Figure 7:
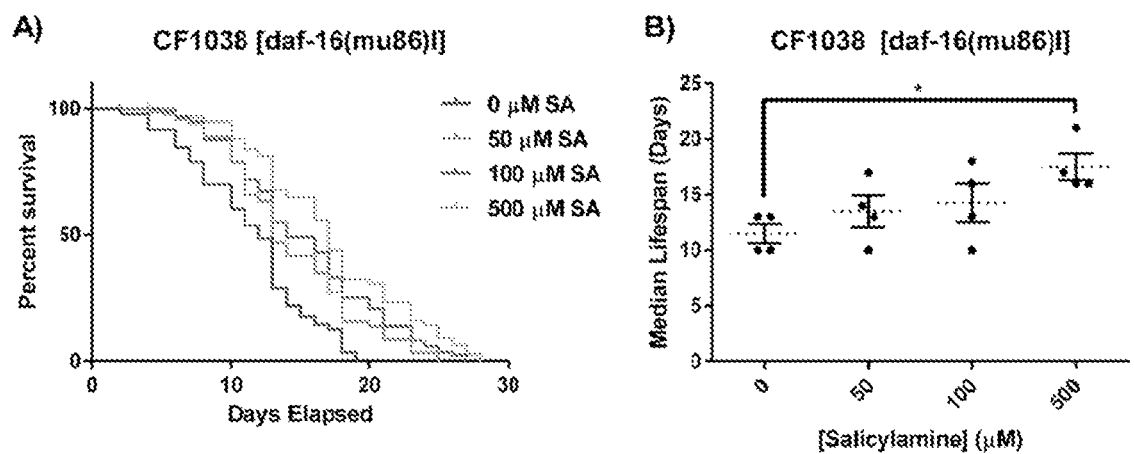
FIG. 7 (S1). SA extends the lifespan of daf-16 gene knockout mutant strain. (A) Kaplan-Meier survival curves depicting effects of SA administration on daf-16 gene knockout mutant strain. Starting at day 1 of adulthood, animals were transferred to OP50-seeded NGM-SA plates every 2 days. Survival was assessed every 2 days until all the worms died. (B) Summary of SA treated daf-16 knockout mutant median lifespans. SA increased maximum and median lifespan in daf-16 knockout worms. Data are expressed as means±SEM from four independent experiments. *P<0.01 as compared to vehicle control.
Figure 8:
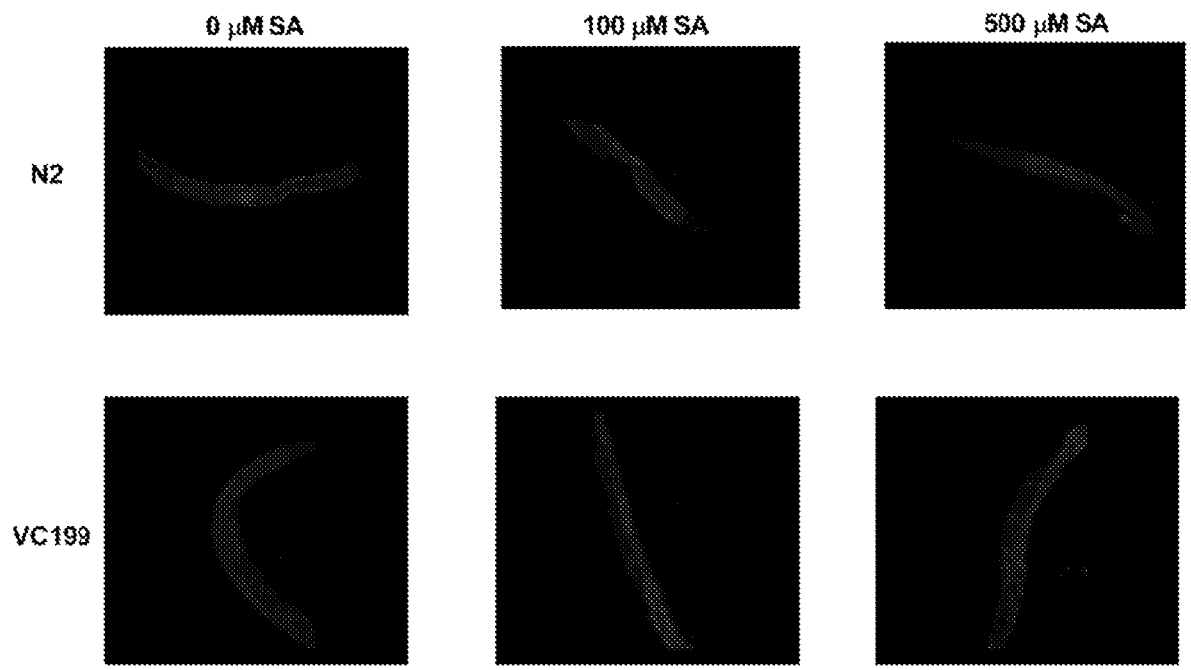
FIG. 8 (S2). Change in lipofuscin autofluorescence with age. (A) Representative confocal images are shown from four experiments. Synchronized late L4/early young adult worms were plated on FUDR containing SA-OP50-seeded NGM plates and worms were maintained at 20° C. Every fifth day, 10-15 worms were mounted onto 2% agar pads and anesthetized with 3 mM levamisole in DMSO. Representative confocal images of each treatment condition were captured through Plan-Aprochromat 20× objective on an LSM510 confocal microscope (Carl Zeiss MicroImaging, Inc) scanning every 200 nm for XZ sections. Images were processed with the Zeiss LSM Image Browser. Figure S2 relates to FIGS. 1C and 3D.
Figure 9:
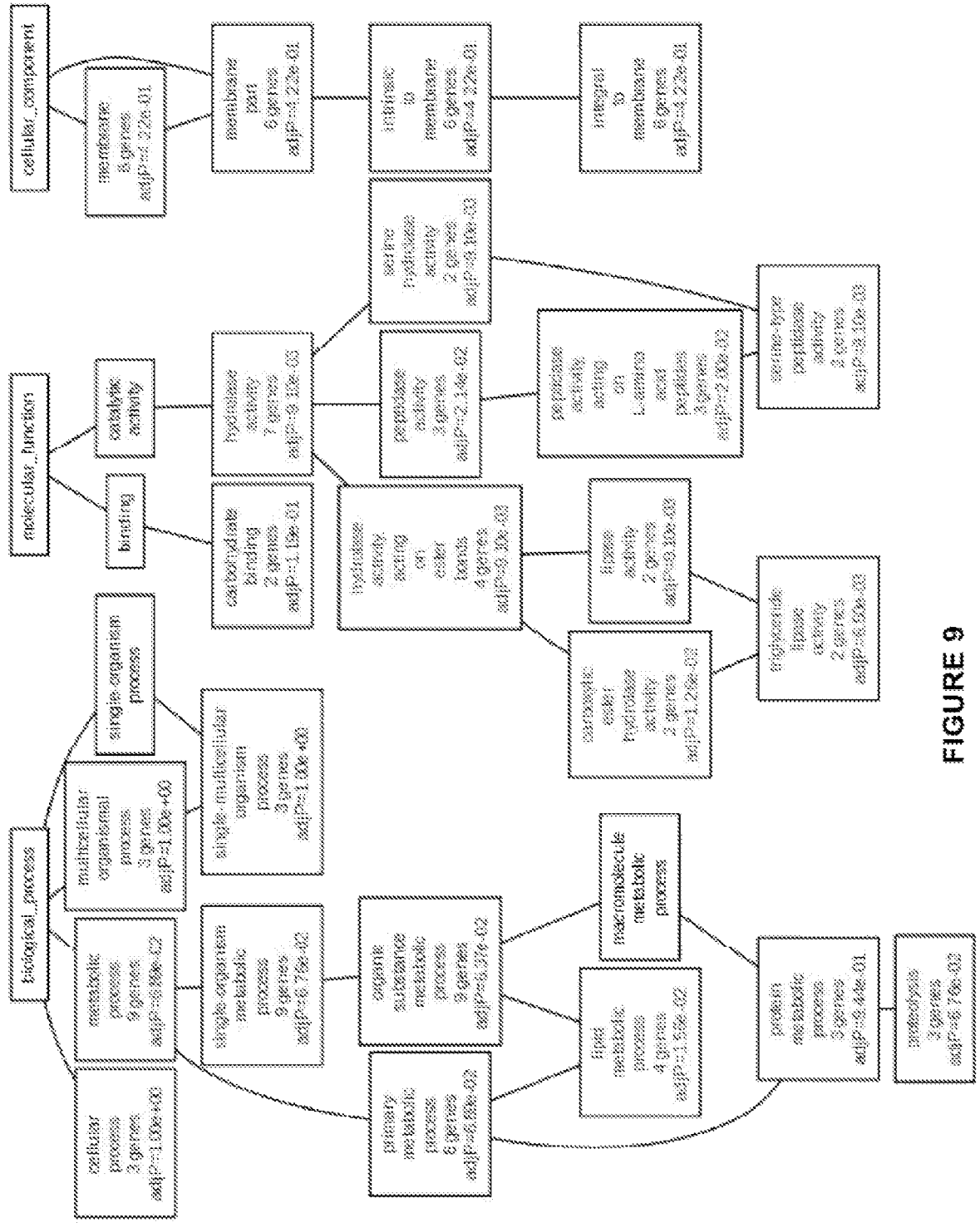
FIG. 9 (S3). Gene Ontology enrichment via WEBGESTALT. Pathway analysis of SA-mediated genomic changes in day 15 N2 WT worms. To further explore the genomic effects of SA administration on N2 WT worms, Gene Ontology (GO) enrichment was performed using WebGestalt, an approach which incorporates information from different public resources and provides graphical depiction of large gene sets from functional genomic, proteomic, and large-scale genetic studies. Biological relationships among Directed acyclic graphs (DAG) were generated using GOView, a web-based application to allow users to visualize and compare multiple provided GO term lists to identify common and specific biological themes. (A) DAG of Group I genes upregulated by SA administration. Chart highlights the metabolic process, lipid metabolic process, and proteolysis pathways among many others as being altered favorably by SA administration.

References and publications cited herein, including those listed below, are incorporated herein by reference.

1. Gardner, H. W., *Oxygen radical chemistry of polyunsaturated fatty acids*. Free Radic Biol Med, 1989. 7(1): p. 65-86.
2. Niki, E., *Lipid peroxidation: physiological levels and dual biological effects*. Free Radic Biol Med, 2009. 47(5): p. 469-84.
3. Halliwell, B. and J. M. Gutteridge, *Role of free radicals and catalytic metal ions in human disease: an overview*. Methods Enzymol, 1990. 186: p. 1-85.
4. Gutteridge, J. M., *Lipid peroxidation and antioxidants as biomarkers of tissue damage*. Clin Chem, 1995. 41(12 Pt 2): p. 1819-28.
5. Butterfield, D. A., *beta-Amyloid-associated free radical oxidative stress and neurotoxicity: implications for Alzheimer's disease*. Chem Res Toxicol, 1997. 10(5): p. 495-506.
6. Poon, H. F., et al., *Free radicals and brain aging*. Clin Geriatr Med, 2004. 20(2): p. 329-59.
7. Comporti, M., *Lipid peroxidation and biogenic aldehydes: from the identification of 4-hydroxynonenal to further achievements in biopathology*. Free Radic Res, 1998. 28(6): p. 623-35.
8. Morrow, J. D., et al., *A series of prostaglandin F2-like compounds are produced in vivo in humans by a non-cyclooxygenase, free radical-catalyzed mechanism*. Proc Natl Acad Sci USA, 1990. 87(23): p. 9383-7.
9. Brame, C. J., et al., *Identification of extremely reactive gamma-ketoaldehydes (isolevuglandins) as products of the isoprostane pathway and characterization of their lysyl protein adducts*. J Biol Chem, 1999. 274(19): p. 13139-46.
10. Boutaud, O., et al., *Characterization of the lysyl adducts formed from prostaglandin H2 via the levuglandin pathway*. Biochemistry, 1999. 38(29): p. 9389-96.
11. Iyer, R. S., S. Ghosh, and R. G. Salomon, *Levuglandin E2 crosslinks proteins*. Prostaglandins, 1989. 37(4): p. 471-80.
12. Salomon, R. G., et al., *Isolevuglandin-protein adducts in humans: products of free radical-induced lipid oxidation through the isoprostane pathway*. Biochim Biophys Acta, 2000. 1485(2-3): p. 225-35.
13. Zagol-Ikapitte, I., et al., *Prostaglandin H(2)-derived adducts of proteins correlate with Alzheimer's disease severity*. J Neurochem, 2005. 94(4): p. 1140-5.
14. Kirabo, A., et al., *DC isoketal-modified proteins activate T cells and promote hypertension*. J Clin Invest, 2014. 124(10): p. 4642-56.
15. Davies, S. S., et al., *Effects of reactive gamma-ketoaldehydes formed by the isoprostane pathway (isoketals) and cyclooxygenase pathway (levuglandins) on proteasome function*. Faseb j, 2002. 16(7): p. 715-7.
16. Boutaud, O., et al., *Prostaglandin H2 (PGH2) accelerates formation of amyloid beta1-42 oligomers*. J Neurochem, 2002. 82(4): p. 1003-6.
17. Murthi, K. K., R. G. Salomon, and H. Sternlicht, *Levuglandin E2 inhibits mitosis and microtubule assembly*. Prostaglandins, 1990. 39(6): p. 611-22.
18. Schmidley, J. W., et al., *Brain tissue injury and blood-brain barrier opening induced by injection of LGE2 or PGE2*. Prostaglandins Leukot Essent Fatty Acids, 1992. 47(2): p. 105-10.
19. Amarnath, V., et al., *Pyridoxamine: An Extremely Potent Scavenger of 1, 4-Dicarbonyls*. Chemical Research in Toxicology, 2004. 17(3): p. 410-415.
20. Davies, S. S., et al., *Pyridoxamine analogues scavenge lipid-derived gamma-ketoaldehydes and protect against H2O2-mediated cytotoxicity*. Biochemistry, 2006. 45(51): p. 15756-67.
21. Zagol-Ikapitte, I., et al., *Determination of the Pharmacokinetics and Oral Bioavailability of Salicylamine, a*

Potent γ-Ketoaldehyde Scavenger, by LC/MS/MS. Pharmaceutics, 2010. 2(1): p. 18.
22. Davies, S. S., et al., *Treatment with a γ-ketoaldehyde scavenger prevents working memory deficits in hApoE4 mice.* Journal of Alzheimer's Disease, 2011. 27(1): p. 49-59.
23. Rose, M. R., et al., *What is Aging?* Frontiers in Genetics, 2012. 3: p. 134.
24. Jin, K., *Modern Biological Theories of Aging.* Aging and Disease, 2010. 1(2): p. 72-74.
25. Kirkwood, T. B., *Understanding the odd science of aging.* Cell, 2005. 120(4): p. 437-47.
26. Wilkinson, D. S., R. C. Taylor, and A. Dillin, *Analysis of aging in Caenorhabditis elegans.* Methods Cell Biol, 2012. 107: p. 353-81.
27. Flat, T., *A new definition of aging?* Front Genet, 2012. 3: p. 148.
28. Murshid, A., T. Eguchi, and S. K. Calderwood, *Stress proteins in aging and life span.* Int J Hyperthermia, 2013. 29(5): p. 442-7.
29. Haigis, M. C. and B. A. Yankner, *The aging stress response.* Mol Cell, 2010. 40(2): p. 333-44.
30. Lockshin, R. A. and J. Beaulaton, *Programmed cell death.* Life Sci, 1974. 15(9): p. 1549-65.
31. Forciea, M. A., *Aging. Programmed change.* Dent Clin North Am, 1989. 33(1): p. 19-22.
32. Gladyshev, V. N., *The Free Radical Theory of Aging Is Dead. Long Live the Damage Theory!* Antioxidants & Redox Signaling, 2014. 20(4): p. 727-731.
33. Comfort, A., *Physiology, homoeostasis and ageing.* Gerontologia, 1968. 14(4): p. 224-34.
34. Hartl, F. U., *Cellular Homeostasis and Aging.* Annu Rev Biochem, 2016.
35. Lints, F. A., *The rate of living theory revisited.* Gerontology, 1989. 35(1): p. 36-57.
36. Brys, K., J. R. Vanfleteren, and B. P. Braeckman, *Testing the rate-of-living/oxidative damage theory of aging in the nematode model Caenorhabditis elegans.* Exp Gerontol, 2007. 42(9): p. 845-51.
37. Harman, D., *Aging: a theory based on free radical and radiation chemistry.* J Gerontol, 1956. 11(3): p. 298-300.
38. Labbadia, J. and R. I. Morimoto, *The Biology of Proteostasis in Aging and Disease.* Annual review of biochemistry, 2015. 84: p. 435-464.
39. Maynard, S., et al., *DNA Damage, DNA Repair, Aging, and Neurodegeneration.* Cold Spring Harb Perspect Med, 2015. 5(10).
40. Donmez, G. and L. Guarente, *Aging and disease: connections to sirtuins.* Aging Cell, 2010. 9(2): p. 285-90.
41. Lin, S. J., P. A. Defossez, and L. Guarente, *Requirement of NAD and SIR2 for life-span extension by calorie restriction in Saccharomyces cerevisiae.* Science, 2000. 289(5487): p. 2126-8.
42. Bell, E. L. and L. Guarente, *The SirT3 divining rod points to oxidative stress.* Mol Cell, 2011. 42(5): p. 561-8.
43. Kaeberlein, M., M. McVey, and L. Guarente, *The SIR2/3/4 complex and SIR2 alone promote longevity in Saccharomyces cerevisiae by two different mechanisms.* Genes Dev, 1999. 13(19): p. 2570-80.
44. Guarente, L., *Sir2 links chromatin silencing, metabolism, and aging.* Genes Dev, 2000. 14(9): p. 1021-6.
45. Tissenbaum, H. A. and L. Guarente, *Increased dosage of a sir-2 gene extends lifespan in Caenorhabditis elegans.* Nature, 2001. 410(6825): p. 227-30.
46. Rogina, B. and S. L. Helfand, *Sir2 mediates longevity in the fly through a pathway related to calorie restriction.* Proc Natl Acad Sci USA, 2004. 101(45): p. 15998-6003.
47. Hashimoto, Y., S. Ookuma, and E. Nishida, *Lifespan extension by suppression of autophagy genes in Caenorhabditis elegans.* Genes Cells, 2009. 14(6): p. 717-26.
48. Lee, G. D., et al., *Dietary deprivation extends lifespan in Caenorhabditis elegans.* Aging Cell, 2006. 5(6): p. 515-24.
49. Wang, Y. and H. A. Tissenbaum, *Overlapping and distinct functions for a Caenorhabditis elegans SIR2 and DAF-16/FOXO.* Mech Ageing Dev, 2006. 127(1): p. 48-56.
50. Bansal, A., et al., *Uncoupling lifespan and healthspan in Caenorhabditis elegans longevity mutants.* Proc Natl Acad Sci USA, 2015. 112(3): p. E277-86.
51. Clokey, G. V. and L. A. Jacobson, *The autofluorescent "lipofuscin granules" in the intestinal cells of Caenorhabditis elegans are secondary lysosomes.* Mech Ageing Dev, 1986. 35(1): p. 79-94.
52. Yin, D., *Biochemical basis of lipofuscin, ceroid, and age pigment-like fluorophores.* Free Radic Biol Med, 1996. 21(6): p. 871-88.
53. Wolkow, C. A., *Identifying factors that promote functional aging in Caenorhabditis elegans.* Exp Gerontol, 2006. 41(10): p. 1001-6.
54. Huang, C., C. Xiong, and K. Kornfeld, *Measurements of age-related changes of physiological processes that predict lifespan of Caenorhabditis elegans.* Proc Natl Acad Sci USA, 2004. 101(21): p. 8084-9.
55. Herndon, L. A., et al., *Stochastic and genetic factors influence tissue-specific decline in ageing C. elegans.* Nature, 2002. 419(6909): p. 808-14.
56. Davies, S. S., et al., *Measurement of chronic oxidative and inflammatory stress by quantification of isoketal/levuglandin gamma-ketoaldehyde protein adducts using liquid chromatography tandem mass spectrometry.* Nat Protoc, 2007. 2(9): p. 2079-91.
57. Zhu, A. Y., et al., *Plasmodium falciparum Sir2A preferentially hydrolyzes medium and long chain fatty acyl lysine.* ACS Chemical Biology, 2012. 7(1): p. 155-159.
58. Choudhary, C., et al., *The growing landscape of lysine acetylation links metabolism and cell signalling.* Nat Rev Mol Cell Biol, 2014. 15(8): p. 536-50.
59. Bokov, A., A. Chaudhuri, and A. Richardson, *The role of oxidative damage and stress in aging.* Mech Ageing Dev, 2004. 125(10-11): p. 811-26.
60. Tao, R., et al., *Sirt3-mediated deacetylation of evolutionarily conserved lysine 122 regulates MnSOD activity in response to stress.* Mol Cell, 2010. 40(6): p. 893-904.
61. Someya, S., et al., *Sirt3 mediates reduction of oxidative damage and prevention of age-related hearing loss under caloric restriction.* Cell, 2010. 143(5): p. 802-12.
62. Caito, S., et al., *SIRT1 is a redox-sensitive deacetylase that is post-translationally modified by oxidants and carbonyl stress.* The FASEB Journal, 2010. 24(9): p. 3145-3159.
63. Nguyen, T. T. and M. Aschner, *F3-Isoprostanes as a Measure of in vivo Oxidative Damage in Caenorhabditis elegans.* Curr Protoc Toxicol, 2014. 62: p. 11.17.1-11.17.13.
64. Labuschagne, C. F., et al., *Quantification of in vivo oxidative damage in Caenorhabditis elegans during aging by endogenous F3-isoprostane measurement.* Aging Cell, 2013. 12(2): p. 214-23.
65. Gao, L., et al., *Formation of F-ring isoprostane-like compounds (F3-isoprostanes) in vivo from eicosapentaenoic acid.* J Biol Chem, 2006. 281(20): p. 14092-9.

66. Wallace, D. C., *A mitochondrial paradigm of metabolic and degenerative diseases, aging, and cancer: a dawn for evolutionary medicine.* Annu Rev Genet, 2005. 39: p. 359-407.
67. Finkel, T. and N. J. Holbrook, *Oxidants, oxidative stress and the biology of ageing.* Nature, 2000. 408(6809): p. 239-47.
68. Ryan, M. T. and N. J. Hoogenraad, *Mitochondrial-nuclear communications.* Annu Rev Biochem, 2007. 76: p. 701-22.
69. Gershon, H. and D. Gershon, *Paradigms in aging research: a critical review and assessment.* Mech Ageing Dev, 2000. 117(1-3): p. 21-8.
70. Alic, N., et al., *Interplay of dFOXO and two ETS-family transcription factors determines lifespan in Drosophila melanogaster.* PLoS Genet, 2014. 10(9): p. e1004619.
71. Thyagarajan, B., et al., *ETS-4 is a transcriptional regulator of life span in Caenorhabditis elegans.* PLoS Genet, 2010. 6(9): p. e1001125.
72. Chin, R. M., et al., *The metabolite alpha-ketoglutarate extends lifespan by inhibiting ATP synthase and TOR.* Nature, 2014. 510(7505): p. 397-401.
73. Rauthan, M., et al., *A Mutation in Caenorhabditis elegans NDUF-7 Activates the Mitochondrial Stress Response and Prolongs Lifespan via ROS and CED-4.* G3 (Bethesda), 2015. 5(8): p. 1639-48.
74. McCormack, S., et al., *Pharmacologic targeting of sirtuin and PPAR signaling improves longevity and mitochondrial physiology in respiratory chain complex I mutant Caenorhabditis elegans.* Mitochondrion, 2015. 22: p. 45-59.
75. Edwards, C., et al., *Mechanisms of amino acid-mediated lifespan extension in Caenorhabditis elegans.* BMC Genet, 2015. 16: p. 8.
76. Furuhashi, T., et al., *1-arginine, an active component of salmon milt nucleoprotein, promotes thermotolerance via Sirtuin in Caenorhabditis elegans.* Biochem Biophys Res Commun, 2016. 472(1): p. 287-91.
77. Pant, A., et al., *Beta-caryophyllene modulates expression of stress response genes and mediates longevity in Caenorhabditis elegans.* Exp Gerontol, 2014. 57: p. 81-95.
78. Guo, X. and L. R. Garcia, *SIR-2.1 integrates metabolic homeostasis with the reproductive neuromuscular excitability in early aging male Caenorhabditis elegans.* Elife, 2014. 3: p. e01730.
79. Calabrese, E. J., et al., *What is hormesis and its relevance to healthy aging and longevity?* Biogerontology, 2015. 16(6): p. 693-707.
80. Monaghan, P. and M. F. Haussmann, *The positive and negative consequences of stressors during early life.* Early Hum Dev, 2015. 91(11): p. 643-7.
81. Sun, S., et al., *Translational profiling identifies a cascade of damage initiated in motor neurons and spreading to glia in mutant SOD1-mediated ALS.* Proceedings of the National Academy of Sciences of the United States of America, 2015. 112(50): p. E6993-E7002.
82. McMaster, W. G., et al., *Inflammation, Immunity, and Hypertensive End-Organ Damage.* Circulation research, 2015. 116(6): p. 1022-1033.
83. Wu, J., et al., *Immune activation caused by vascular oxidation promotes fibrosis and hypertension.* J Clin Invest, 2016. 126(1): p. 50-67.
84. Egnatchik, R. A., Brittain, Evan, Shah, Amy T., Fares, Wassim H., Ford, H. James, Monahan, Ken, Kang, Christie J., Kocurek, Emily G., Nguyen, Thuy T., Zhu, Shijun, Hysinger, Erik, Austin, Eric, Skala, Melissa C., Young, Jamey D., Roberts II, L. Jackson, Hamnes, Anna R., West, James, Fessel, Joshua P., *Loss of normal Bone Morphogenetic Protein Receptor Type 2 signaling drives pulmonary hypertension through metabolic reprogramming toward glutaminolysis.* In Press, 2016.
85. Wang, H., et al., *NRF2 activation by antioxidant antidiabetic agents accelerates tumor metastasis.* Sci Transl Med, 2016. 8(334): p. 334ra51.
86. Prasad, S., S. C. Gupta, and A. K. Tyagi, *Reactive oxygen species (ROS) and cancer: Role of antioxidative nutraceuticals.* Cancer Lett, 2016.
87. Lewis, J. A. and J. T. Fleming, *Basic culture methods.* Methods Cell Biol, 1995. 48: p. 3-29.
88. Mitchell, D. H., et al., *Synchronous growth and aging of Caenorhabditis elegans in the presence of fluorodeoxyuridine.* J Gerontol, 1979. 34(1): p. 28-36.
89. Gavet, O. and J. Pines, *Progressive activation of CyclinB1-Cdk1 coordinates entry to mitosis.* Developmental cell, 2010. 18(4): p. 533-543.
90. Bratic, I., et al., *Mitochondrial DNA level, but not active replicase, is essential for Caenorhabditis elegans development.* Nucleic Acids Res, 2009. 37(6): p. 1817-28.
91. Amarnath, V., et al., *A Simplified Synthesis of the Diastereomers of Levuglandin E2.* Synthetic Communications, 2005. 35(3): p. 397-408.
92. Milne, G. L., et al., *Quantification of F2-isoprostanes as a biomarker of oxidative stress.* Nat Protoc, 2007. 2(1): p. 221-6.
93. Latif, S., et al., *Fluorescence Polarization in Homogeneous Nucleic Acid Analysis II: 5'-Nuclease Assay.* Genome Research, 2001. 11(3): p. 436-440.

The invention thus being described, it would be obvious that the same can be varied in many ways. Such variations that would be obvious to one of ordinary skill in the art is to be considered as being bard of this disclosure.

Unless otherwise indicated, all numbers expressing quantities of ingredients, properties such as reaction conditions, and so forth used in the Specification are to be understood as being modified in all instances by the term "about." Accordingly, unless indicated by the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental sections or the example sections are reported as precisely as possible. Any numerical value, however, inherently contain certain errors necessarily resulting from the standard deviation found in their respective testing measurements.

We claim:

1. A method for slowing the progression of cell death in a subject diagnosed with age-related oxidant injury, comprising:

measuring an isoprostane level in said subject to determine the need for sirtuin modulation; and administering to said subject an effective sirtuin potentiating amount of a compound selected from the formula:

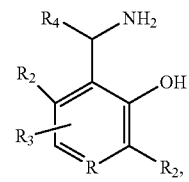

wherein:
R is CH, C—CH$_3$, or C—CH$_2$—CH$_3$;
R$_2$ is independently H, substituted or unsubstituted alkyl;
R$_3$ is H, halogen, alkoxy, hydroxyl, nitro;
R$_4$ is H, substituted or unsubstituted alkyl, carboxyl; and pharmaceutically acceptable salts thereof.

2. The method of claim 1, wherein the compound is selected from:

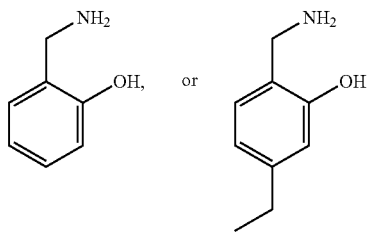

or a pharmaceutically acceptable salt thereof.

3. The method of claim 1, wherein the compound is 2-hydroxybenzylamine, ethyl-2-hydroxybenzylamine, or methyl-2-hydroxybenzylamine; or a pharmaceutically acceptable salt thereof.

4. The method of claim 1, wherein the compound is selected from the following compound,

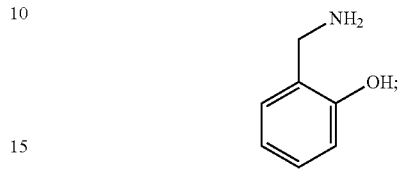

or a pharmaceutically acceptable salt thereof.

* * * * *